United States Patent
Earl et al.

(10) Patent No.: US 12,251,314 B2
(45) Date of Patent: Mar. 18, 2025

(54) PROSTHETIC KNEE IMPLANT SYSTEMS AND METHODS WITH LINKED TIBIAL ROTATION

(71) Applicant: Zimmer, Inc., Warsaw, IN (US)

(72) Inventors: Brian D. Earl, South Bend, IN (US); Alexander P. Wolfe, Fort Wayne, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 18/367,782

(22) Filed: Sep. 13, 2023

(65) Prior Publication Data

US 2024/0000576 A1 Jan. 4, 2024

Related U.S. Application Data

(63) Continuation of application No. 17/137,992, filed on Dec. 30, 2020, now Pat. No. 11,793,650, which is a
(Continued)

(51) Int. Cl.
*A61B 17/56* (2006.01)
*A61F 2/30* (2006.01)
(Continued)

(52) U.S. Cl.
CPC ............ *A61F 2/3868* (2013.01); *A61F 2/384* (2013.01); *A61F 2/3859* (2013.01);
(Continued)

(58) Field of Classification Search
None
See application file for complete search history.

(56) References Cited

U.S. PATENT DOCUMENTS

| 4,211,228 A | 7/1980 | Cloutier |
| 4,759,350 A | 7/1988 | Dunn et al. |

(Continued)

FOREIGN PATENT DOCUMENTS

| CN | 103200903 A | 7/2013 |
| CN | 104042370 A | 9/2014 |

(Continued)

OTHER PUBLICATIONS

"U.S. Appl. No. 15/903,846, Advisory Action mailed Jun. 15, 2020", 3 pgs.

(Continued)

*Primary Examiner* — Ann Schillinger
(74) *Attorney, Agent, or Firm* — Schwegman Lundberg & Woessner, P.A.

(57) ABSTRACT

A tibial spacer paddle comprises a spacer block comprising opposing bearing surfaces, an alignment slot extending into the spacer block; and a handle extending from the spacer block. The spacer block can include feet for passively engaging the femur or pegs for actively engaging a femoral component so that the spacer block is linked to the femur while the tibia rotates. A tibial spacer system comprises a provisional component having an alignment tab extending from a body and an alignment indicator located on the body, a femoral component and a pin extending from the femoral component. The pin can engage the alignment tab so that the provisional component is linked to the femur while the tibia rotates. In addition to or alternatively to the alignment tab and pin, the provisional component can include a tibial plate that can be rotationally connected to the provisional component.

20 Claims, 16 Drawing Sheets

Related U.S. Application Data continuation of application No. 15/903,846, filed on Feb. 23, 2018, now Pat. No. 10,905,560.

(60) Provisional application No. 62/464,076, filed on Feb. 27, 2017.

(51) Int. Cl.
*A61F 2/38* (2006.01)
*A61F 2/46* (2006.01)

(52) U.S. Cl.
CPC .......... *A61F 2/4657* (2013.01); *A61F 2/4684* (2013.01); *A61F 2/30771* (2013.01); *A61F 2/3886* (2013.01); *A61F 2/389* (2013.01); *A61F 2002/4658* (2013.01)

(56) References Cited

U.S. PATENT DOCUMENTS

| | | | |
|---|---|---|---|
| 5,470,354 A * | 11/1995 | Hershberger | A61F 2/4684 600/595 |
| 5,520,695 A | 5/1996 | Luckman | |
| 5,540,696 A * | 7/1996 | Booth, Jr. | A61B 17/025 606/88 |
| 5,634,927 A | 6/1997 | Houston et al. | |
| 5,733,292 A * | 3/1998 | Gustilo | A61B 17/025 606/88 |
| 5,782,925 A * | 7/1998 | Collazo | A61F 2/4684 623/20.28 |
| 6,077,270 A * | 6/2000 | Katz | A61B 17/154 606/88 |
| 7,153,327 B1 * | 12/2006 | Metzger | A61F 2/3868 623/20.29 |
| 8,603,101 B2 | 12/2013 | Claypool et al. | |
| 8,968,412 B2 | 3/2015 | Wogoman et al. | |
| 9,138,238 B2 * | 9/2015 | Sordelet | A61B 17/164 |
| 9,211,189 B2 | 12/2015 | Earl et al. | |
| 9,592,133 B2 * | 3/2017 | Toler | A61B 17/025 |
| 10,154,836 B2 * | 12/2018 | D'Lima | A61B 17/025 |
| 10,166,034 B2 * | 1/2019 | Claypool | A61B 17/155 |
| 10,357,255 B2 * | 7/2019 | Collazo | A61B 17/15 |
| 10,537,439 B2 * | 1/2020 | Wolfson | A61F 2/461 |
| 10,905,560 B2 * | 2/2021 | Earl | A61F 2/4657 |
| 2004/0122441 A1 * | 6/2004 | Muratsu | A61B 17/0206 606/102 |
| 2006/0004374 A1 | 1/2006 | Griner et al. | |
| 2006/0020343 A1 | 1/2006 | Ek | |
| 2006/0200162 A1 | 9/2006 | Farling et al. | |
| 2007/0233138 A1 | 10/2007 | Figueroa et al. | |
| 2008/0177261 A1 * | 7/2008 | McMinn | A61B 17/155 606/62 |
| 2008/0275457 A1 | 11/2008 | Meek et al. | |
| 2009/0149964 A1 * | 6/2009 | May | A61B 17/1764 623/20.29 |
| 2011/0066247 A1 * | 3/2011 | Ries | A61B 17/1764 623/20.27 |
| 2011/0093080 A1 * | 4/2011 | Slone | A61F 2/384 623/20.14 |
| 2012/0022660 A1 | 1/2012 | Wentorf | |
| 2012/0158152 A1 | 6/2012 | Claypool et al. | |
| 2013/0261504 A1 | 10/2013 | Claypool et al. | |
| 2014/0052269 A1 | 2/2014 | Claypool et al. | |
| 2014/0058398 A1 * | 2/2014 | Kaneyama | A61F 2/3836 623/20.14 |
| 2014/0296859 A1 | 10/2014 | Claypool et al. | |
| 2015/0088140 A1 | 3/2015 | Toler et al. | |
| 2015/0335449 A1 | 11/2015 | Ries et al. | |
| 2016/0045205 A1 * | 2/2016 | Metzger | A61F 2/4657 606/88 |
| 2016/0367381 A1 | 12/2016 | Chaney et al. | |
| 2017/0164957 A1 * | 6/2017 | Bojarski | A61B 34/10 |
| 2018/0243101 A1 | 8/2018 | Earl et al. | |
| 2019/0290452 A1 * | 9/2019 | Trabish | A61B 5/4585 |
| 2021/0113341 A1 | 4/2021 | Earl et al. | |

FOREIGN PATENT DOCUMENTS

| | | | |
|---|---|---|---|
| CN | 104379094 A | 2/2015 | |
| CN | 106214293 A | 12/2016 | |
| CN | 110337281 A | 10/2019 | |
| CN | 114010374 A | 2/2022 | |
| EP | 2540256 A1 | 1/2013 | |
| WO | WO-2012018564 A1 | 2/2012 | |
| WO | WO-2017155995 A1 | 9/2017 | |
| WO | WO-2017157767 A1 * | 9/2017 | .......... A61B 17/025 |
| WO | WO-2018156936 A1 | 8/2018 | |

OTHER PUBLICATIONS

"U.S. Appl. No. 15/903,846, Final Office Action mailed Mar. 30, 2020", 19 pgs.
"U.S. Appl. No. 15/903,846, Non Final Office Action mailed Sep. 19, 2019", 12 pgs.
"U.S. Appl. No. 15/903,846, Notice of Allowance mailed Sep. 29, 2020", 8 pgs.
"U.S. Appl. No. 15/903,846, Response filed Jun. 1, 2020 to Final Office Action mailed Mar. 30, 2020", 16 pgs.
"U.S. Appl. No. 15/903,846, Response filed Jun. 29, 2020 to Advisory Action mailed Jun. 15, 2020", 16 pgs.
"U.S. Appl. No. 15/903,846, Response filed Dec. 19, 2019 to Non Final Office Action mailed Sep. 19, 2019", 15 pgs.
"U.S. Appl. No. 15/903,846, Response filed Aug. 26, 2019 to Restriction Requirement mailed Jun. 25, 2019", 7 pgs.
"U.S. Appl. No. 15/903,846, Restriction Requirement mailed Jun. 25, 2019", 8 pgs.
"U.S. Appl. No. 17/137,992, Non Final Office Action mailed Nov. 25, 2022", 9 pgs.
"U.S. Appl. No. 17/137,992, Notice of Allowance mailed Jun. 14, 2023", 7 pgs.
"U.S. Appl. No. 17/137,992, Response filed Feb. 23, 2023 to Non Final Office Action mailed Nov. 25, 2022", 15 pgs.
"U.S. Appl. No. 17/137,992, Response filed Nov. 2, 2022 to Restriction Requirement mailed Oct. 19, 2022", 7 pgs.
"U.S. Appl. No. 17/137,992, Restriction Requirement mailed Oct. 19, 2022", 6 pgs.
"Chinese Application Serial No. 201880014269.1, Office Action mailed Mar. 26, 2021", (W/ English Translation), 14 pgs.
"Chinese Application Serial No. 201880014269.1, Response filed Jul. 13, 2021 to Office Action mailed Mar. 26, 2021", (W/ English Translation), 13 pgs.
"European Application Serial No. 18708882.8, Response to Communication pursuant to Rules 161(1) and 162 EPC filed May 1, 2020", 16 pgs.
"European Application Serial No. 21178328.7, Extended European Search Report mailed Jun. 20, 2022", 10 pgs.
"European Application Serial No. 21178328.7, Partial European Search Report mailed Mar. 17, 2022", 10 pgs.
"International Application Serial No. PCT/US2018/019488, International Preliminary Report on Patentability mailed Sep. 6, 2019", 13 pgs.
"International Application Serial No. PCT/US2018/019488, International Search Report mailed Jul. 24, 2018", 8 pgs.
"International Application Serial No. PCT/US2018/019488, Invitation to Pay Add'l Fees and Partial Search Report mailed May 25, 2018", 14 pgs.
"International Application Serial No. PCT/US2018/019488, Written Opinion mailed Jul. 24, 2018", 11 pgs.
U.S. Appl. No. 15/903,846 U.S. Pat. No. 10,905,560, filed Feb. 23, 2018, Prosthetic Knee Implant Systems and Methods With Linked Tibial Rotation.
U.S. Appl. No. 17/137,992, filed Dec. 30, 2020, Prosthetic Knee Implant Systems and Methods With Linked Tibial Rotation.

* cited by examiner

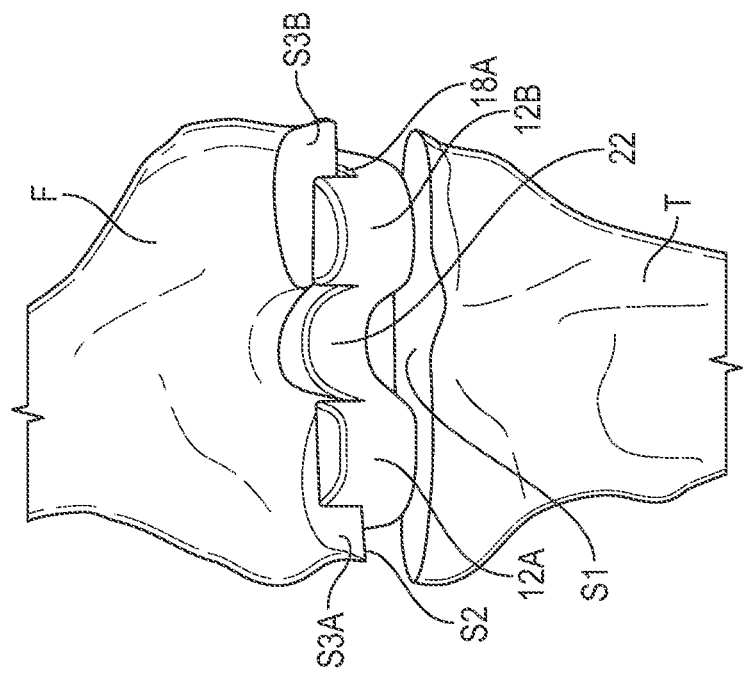
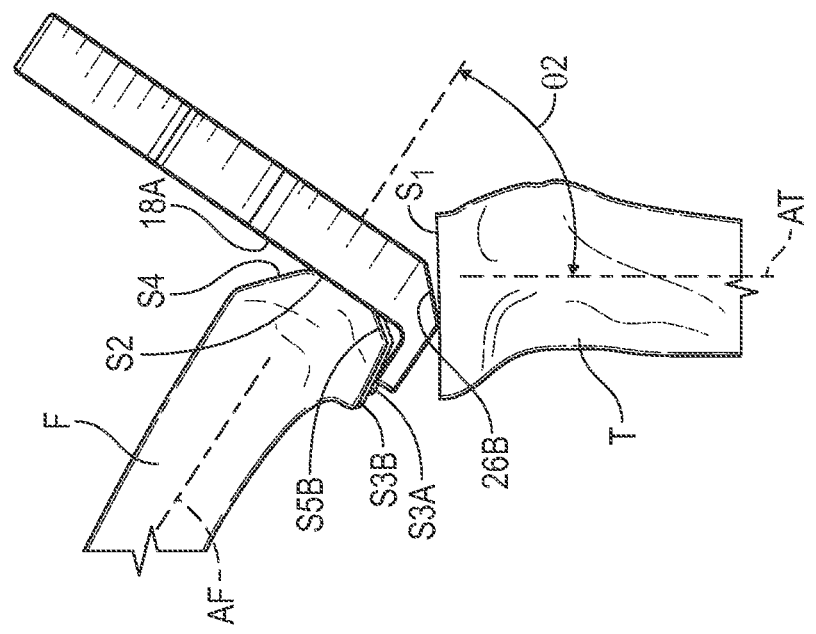
FIG. 4A
FIG. 4B

PROSTHETIC KNEE IMPLANT SYSTEMS AND METHODS WITH LINKED TIBIAL ROTATION

CLAIM OF PRIORITY

This application is a continuation of U.S. application Ser. No. 17/137,992, filed Dec. 30, 2020, which is a continuation of U.S. application Ser. No. 15/903,846, filed Feb. 23, 2018, now issued as U.S. Pat. No. 10,905,560, which claims the benefit of U.S. Provisional Patent Application Ser. No. 62/464,076, filed on Feb. 27, 2017, the benefit of priority of each of which is claimed hereby, and each of which is incorporated by reference herein in its entirety.

TECHNICAL FIELD

This document pertains generally, but not by way of limitation, to orthopedic implant systems and methods for knee arthroplasty. More particularly, this disclosure relates, but not by way of limitation, to orthopedic devices and methods for matching internal/external rotation of a tibial component to that of a femoral component.

BACKGROUND

A natural knee joint typically undergoes a degree of rotation between the tibia and the femur during flexion. Specifically, the femur can rotate in a transverse plane relative 25 to the tibia. Thus, it can be desirable to replicate the natural rotational alignment of the tibia and femur when implanting one or more orthopedic femoral and tibial components.

Frequently the rotation of the tibial component is set independently of the femoral component, and solely based on tibial bony landmarks. In some cases, this can result in mal-rotation of the tibial component with respect to the femoral component. In these cases, if a highly conforming articulation design between femur and tibia is used, when the prosthesis is loaded, the mating tibial-femoral articulating surfaces will drive the tibial component into rotational alignment with the femoral component. This shifting of the tibial component will in turn rotate the entire tibial bone into a non-physiologic orientation with respect to the femur. This can result in pain, stiffness, and a knee that does not feel normal.

Some surgeons have attempted to match natural tibial rotation by a technique called "floating the tibia." In this approach, the femoral trial can be placed and a trial reduction can be performed with the tibial bearing placed in a tibial sizing tray that is free to rotate and translate on the surface of the proximal tibial resection. The tibial sizing tray is thus free to "float" between the resected tibia and the femoral trial. The knee is taken through a range of motion and then out to full extension. The surgeon can then use a pen or Bovie to mark a point on the tibial bone corresponding to the front of the tibial sizing plate. The assumption inherent in this approach is that the conformity between the bearing and the femoral component will force the bearing (and thus the tibial sizing plate) to shift into rotational alignment with the femoral component.

Examples of prosthetic knee implants are described in U.S. Pat. No. 5,782,925 to Collazo et al. and U.S. Pat. No. 9,211,189 to Earl et al.

OVERVIEW

The present inventors have recognized, among other things, that there can be problems associated with attempting to match the natural rotation of the tibia to the femur using the "floating tibia" technique. First, when the knee is taken out to full extension, the tibial component can be under compressive load from the femur which can inhibit relative motion of the tibial component on the tibial bone. Second, contemporary total knee arthroplasty (TKA) articulations can be designed with a measure of rotational laxity. There can be insufficient conformity for the femoral component to drive movement of the tibial component, particularly when it is under compressive load. Third, when the surgeon marks the point on the anterior bone denoting the front of the tibial trial, there is typically no corresponding mark at the posterior tibia to define the axis of rotation. The surgeon can align to the front mark, but needs to estimate where the posterior of the tibial trial was oriented.

The present subject matter can help provide a solution to various problems associated with matching the natural rotation of the tibia to the femur when implanting prosthetic knee components.

In an example, the present subject matter can help provide a solution to these problems, such as by providing a tibial spacer paddle that can comprise a spacer block, first and second feet, first and second alignment chamfers, an alignment slot, and a handle. The spacer block can comprise a first bearing surface, a second bearing surface disposed opposite the first bearing surface, and an edge periphery region connecting the first bearing surface and the second bearing surface. The first foot can extend from the first bearing surface at the edge periphery region. The second foot can extend from the first bearing surface at the edge periphery region spaced from the first foot. The first alignment chamfer can extend into the edge periphery region and the second bearing surface opposite the first foot. The second alignment chamfer can extend into the edge periphery region and the second bearing surface opposite the second foot. The alignment slot can extend into the edge periphery region opposite the first and second feet. The handle can extend from the spacer block.

In another example, a tibial spacer system can comprise a spacer block, a first peg, a second peg, an alignment slot and a handle. The spacer block can comprise a first bearing surface, a second bearing surface disposed opposite the first bearing surface, and an edge periphery region connecting the first bearing surface and the second bearing surface. The first peg can extend from the first bearing surface. The second peg can extend from the first bearing surface spaced from the first peg. The alignment slot can extend into the edge periphery region. The handle can extend from the spacer block.

In yet another example, a tibial spacer system can comprise a provisional component and a sizing extension. The provisional component can comprise a body, an articulating surface positioned on the body configured to engage condylar surfaces of a femoral component, and an alignment tab extending from the body. The sizing extension can extend from the body opposite the articulating surface. The sizing extension can comprise a bone engagement surface, an edge periphery region extending from the bone engagement surface, and a first alignment indicator located on the edge periphery region of the sizing extension.

In still another example, a tibial spacer system can comprise a provisional component, a trial bearing and a pivot coupling. The provisional component can comprise an articulating surface configured to engage condylar surfaces of a femoral component, a first bearing surface disposed opposite the articulating surface, and a first edge periphery region connecting the articulating surface and the first bearing surface. The trial bearing can comprise a bone engagement surface, a second bearing surface disposed opposite the bone engagement surface, and a second edge periphery region connecting the bone engagement surface and the second bearing surface. The pivot coupling can connect the first bearing surface and the second bearing surface. The pivot coupling can be configured to permit the trial bearing to rotate relative to the provisional component.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

FIG. 4A is a side view of the tibial spacer paddle of FIGS. 1-3 inserted between a resected tibia and a resected femur in approximately sixty degrees of flexion.

FIG. 4B is a posterior view of the tibial spacer paddle of FIG. 4A showing the alignment feet engaged with posterior resected surfaces of the femur.

DETAILED DESCRIPTION

Figure 1:
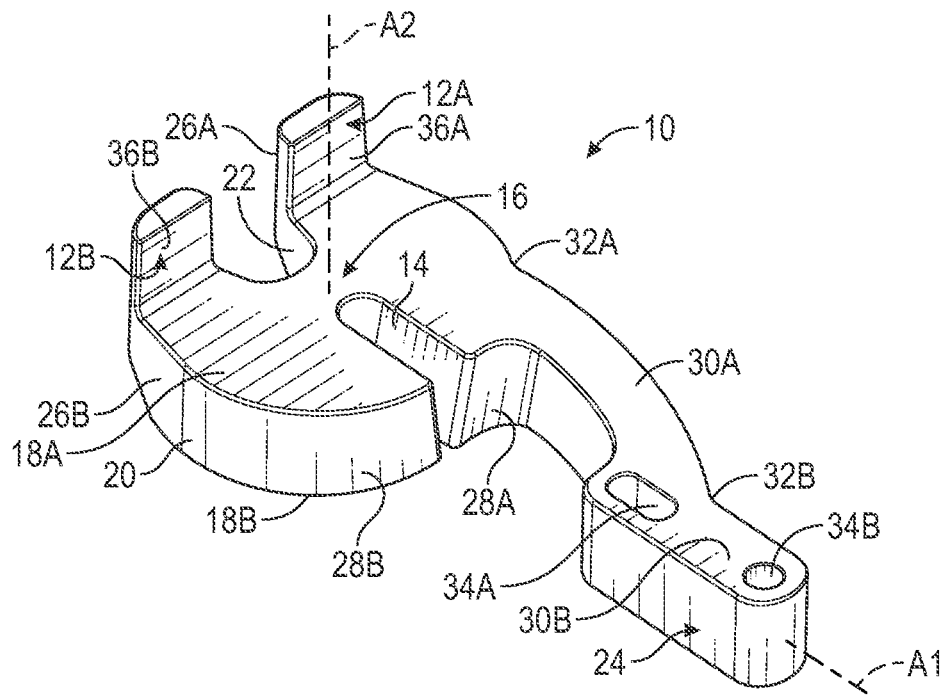
FIG. 1 is a perspective view of a tibial spacer paddle having alignment feet and an indicator groove.
Figure 2:
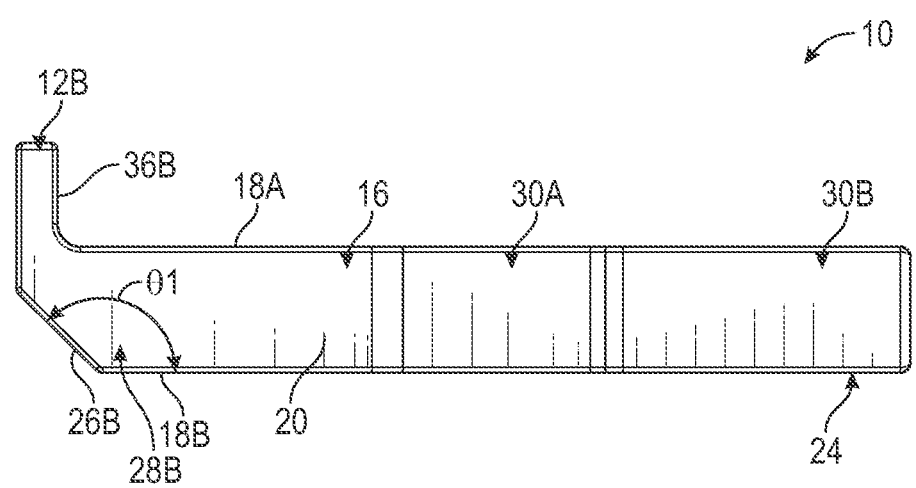
FIG. 2 is a side view of the tibial spacer paddle of FIG. 1 showing an angle of the 10 alignment feet relative to a bearing surface.
Figure 3:
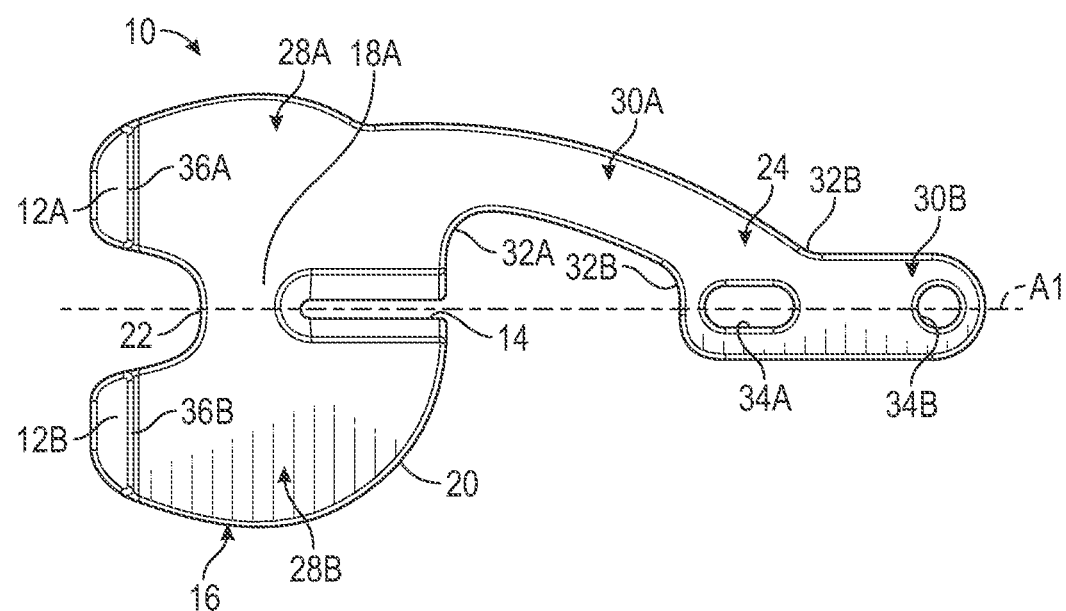
FIG. 3 is a top view of the tibial spacer paddle of FIG. 1 showing a location for the indicator groove.

FIG. 1 is a perspective view of tibial spacer paddle 10 having alignment feet 12A and 12B and indicator groove 14 disposed in spacer block 16. FIG. 2 is a side view of tibial spacer paddle 10 of FIG. 1 showing an angle of alignment feet 12A and 12B relative to bearing surface 18A. FIG. 3 is a top view of the tibial spacer paddle of FIG. 1 showing a location for the indicator groove 14. FIGS. 1-3 are discussed concurrently.

Spacer block 16 can include first bearing surface 18A, second bearing surface 18B, edge periphery surface 20, notch 22 and handle 24. Edge periphery surface 20 can include chamfers 26A and 26B opposite alignment feet 12A and 12B, respectively. Notch 22 and indicator groove 14 can extend into spacer block 16 to form first condylar portion 28A and second condylar portion 28B. Handle 24 can extend from edge periphery surface 20 of spacer block 16 and can include first segment 30A and second segment 30B.

Spacer block 16 is configured to be inserted or otherwise disposed between surfaces, particularly resected surfaces, of a tibia and femur, as shown in FIGS. 4A-4E. First bearing surface 18A can be configured to face toward a tibia and second bearing surface 18B can be configured to face toward a femur. First segment 28A and second segment 28B can be configured to align with condyles of the femur. Edge periphery surface 20 can be shaped so that first segment 28A and second segment 28B can engage medial and lateral condyles of left and right leg femurs. In other examples, spacer block 16 can be configured specifically for a left or right leg knee. As will be discussed in greater detail below with reference to FIGS. 4A-4F, indicator groove 14 can provide an indication of the rotational alignment between the tibia and the femur as the tibia moves through extension and flexion in order to provide alignment information for implantation of prosthetic femoral and tibial components.

Alignment feet 12A and 12B can be located at edges of first segment 28A and second segment 28B, respectively, of bearing surface 18A so as to extend from edge periphery surface 20. In examples, alignment feet 12A and 12B are positioned to be located at a posterior side of the tibia and femur. Chamfers 26A and 26B are disposed opposite feet 12A and 12B, respectively, in bearing surface 18B and remove a portion of spacer block 16 at edge periphery surface 20 so that the tibia can be rotated against second bearing surface 18B. Notch 22 can extend between first segment 28A and second segment 28B in order to provide visibility of the tibia. In an example, chamfers 26A and 26B can form an angle θ1 (FIG. 2) with bearing surface 18B of approximately one-hundred-thirty-five degrees.

Handle 24 can extend from edge periphery surface 20 to provide structure for a surgeon to handle and manipulate spacer block 16. Handle 24 can extend from an anterior portion of spacer block 16 so that tibial spacer paddle 10 can be inserted into an incision in an anterior portion of a knee joint. If desired, an instrument, such as a retractor, can be used to hold tibia T and femur F in a retracted position to allow for insertion of tibial spacer paddle 10. Handle 24 can extend from edge periphery surface 20 offset from a center of spacer block 16 to provide space for placement of indicator groove 14, which can be placed at the center of spacer block 16. First segment 30A of handle 24 can extend from second portion 28B of spacer block 16 at posterior end 32A. First segment 30A can be curved toward indicator groove 14 so that anterior end 32B is brought closer to indicator groove 14. Second segment 30B can be attached to anterior end 32B so that second segment 30B substantially aligns with alignment slot 14.

Anterior end 32B can be planar and can extend parallel to indicator groove 14. Second segment 30B can comprise an elongate body having a central axis A1 that is configured to extend axially in the direction of indicator groove 14. Handle 24 therefore provides an indication of the center of spacer block 16 and points in the direction of indicator groove 14 to provide a surgeon with tactile indicator for the orientation of tibial spacer paddle 10. Second segment 30B can include access bores 34A and 34B that can provide various functions, such as to allow tools or instruments to be inserted through handle 24.

Bearing surface 18A can be configured to face a resected tibia surface. Bearing surface 18B can be configured to face a resected femur surface. The resected tibia and femur surfaces can be planar or nearly planar. Bearing surfaces 18A and 18B can also be planar or nearly planar so as to readily slide against the resected tibia and femur surfaces. Indicator groove 14 can extend all the way through spacer block 16 from first bearing surface 18A to second bearing surface 18B so that the resected tibia can be accessed through indicator groove 14. Indicator groove 14 can be tapered between first bearing surface 18A and second bearing surface 18B. Indicator groove 14 can be wider at first bearing surface 18A than at second bearing surface 18B. As such, indicator surface can be configured to guide an instrument, such as a pen, Bovie, marker, scalpel or pick, toward the tibia. The greater width of indicator groove 14 at first bearing surface 18A can facilitate insertion of the instrument by a surgeon into indicator groove 14, while the narrower width of indicator groove 14 at second bearing surface 18B can facilitate guidance of the instrument to a more precise location on the tibia.

Figure 4C:
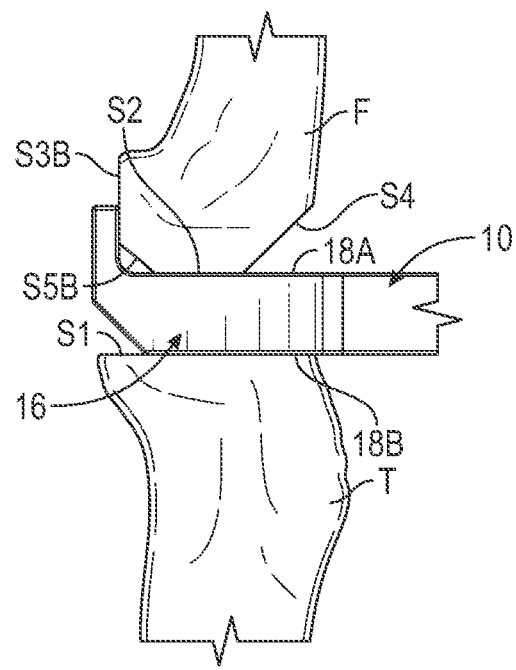
FIG. 4C is a side view of the tibial spacer paddle of FIG. 4A shown with the tibia in full extension.

Alignment feet 12A and 12B can be configured to hold spacer block 16 into engagement with the resected femur. Posterior surfaces 36A and 36B can extend from first bearing surface 18A at right angles or near right angles. However, in other examples, posterior surfaces 36A and 36B can extend at other angles relative to bearing surface 18A for use with surgical procedures where the resected femur surface is not perpendicular to a resected flat anterior surface of the femur (as shown in FIG. 4A). Thus, bearing surface 18A can remain engaged with a distal resected surface of the femur while posterior surfaces 36A and 36B can remain engaged with posterior resected surfaces of the femur. If desired, a surgeon can grasp handle 24 to facilitate engagement of spacer block 16 and the femur. As the tibia moves from flexion to extension, the tibia can rotate against bearing surface 18B along vertical axis A2, as described in greater detail with reference to FIGS. 4A-4F.

FIG. 4A is a side view of tibial spacer paddle 10 of FIGS. 1-3 inserted between resected tibia T and resected femur F in approximately sixty degrees of flexion as defined by angle θ2. Resected tibia T can include proximal surface S1. Resected femur F can include distal surface S2, first posterior surface S3A, second posterior surface S3B, angled anterior surface S4, first quarter surface S5A and second quarter surface S5B. Tibia T and femur F can be resected using any conventional resection process. Tibial spacer paddle 10 depicted in FIGS. 1-3 is configured to be used with the resected surfaces shown in FIGS. 4A-4F. However, tibial spacer paddle 10 can be used with other resections. Additionally, tibial spacer paddle 10 can modified to be used with other resections. Tibial spacer paddle 10 can be configured in various embodiments to allow rotation of one of tibia T and femur F against tibial spacer paddle 10 while having surfaces that permit tibial spacer paddle 10 to be held in flush engagement with the other of tibia T and femur F.

With tibia T and femur F in flexion, tibial spacer paddle 10 can be inserted between distal surface S2 of Femur F and proximal surface S1 of tibia T. For example, tibia T and femur F can be positioned into approximately sixty degrees of flexion to receive tibial spacer paddle 10, as defined by angle θ2, between femur axis AF and tibia axis AT. A surgeon can grasp handle 24 to insert spacer block 18 into an incision in a knee of a patient and further into a space between tibia T and femur F. Alignment feet 12A and 12B can be slipped around distal surface S2 to engage first and second posterior surfaces S3A and S3B. Bearing surface 18A can be positioned against distal surface S2. Chamfers 26A and 26B can be positioned to contact proximal surface S1. With femur F and tibia T disposed in sixty degrees of flexion, as shown in FIG. 4A, chamfers 26A and 26B will be slightly canted with respect to proximal surface S1 such that an edge of chamfers 26A and 26B and edge periphery surface 20 is engaged with proximal surface S1. In other words, if femur F and tibia T were disposed in forty-five degrees of flexion, chamfers 26A and 26B would be flush with proximal surface S1 due to angle θ1 being one-hundred-thirty-five degrees.

FIG. 4B is a posterior view of the tibial spacer paddle 10 of FIG. 4A showing alignment feet 12A and 12B engaged with first posterior surface S3A and second posterior surface S3B of femur F. Notch 22 is shown between feet 12A and 12B and shows proximal surface S1 therebetween. Bearing surface 18A is shown engaged with distal surface S2. As such, feet 12A and 12B can be rotated on proximal surface S1 as tibia T rotates relative to femur F as tibia T and femur F move between extension and flexion. Tibial spacer paddle 10 can remain engaged with tibia T due to pressure applied by tendons and ligaments connecting tibia T and femur F.

FIG. 4C is a side view of tibial spacer paddle 10 of FIG. 4A shown with tibia T in full extension. As tibia T moves into full extension from the flexion position of FIG. 4B, tibia T rotates so that bearing surface 18B engages proximal surface S1 of tibia T. With bearing surface 18A already engaged flush with distal surface S1, spacer block 16 can be positioned squarely between distal surface S1 and proximal surface S1. Feet 12A and 12B keep the rotational orientation of tibial spacer paddle 10 constant with respect to the axis of femur F, thereby allowing tibia T to rotate along the axis of tibia T against bearing surface 18B as tibia T moves into extension. Indicator groove 14 points to a portion of tibia T that shows where the center of femur F points to on proximal surface S1, thus showing the natural rotational position of tibia T relative to femur F.

Spacer block 16 can have a thickness between bearing surface 18A and bearing surface 18B that can be matched to various prosthetic devices. For example, the thickness can be equal to the total thickness of a femoral component and a tibial component intended to be implanted on femur F and tibia T, respectively. The thickness of spacer block 16 can allow the ligaments and tendons of femur F and tibia T to hold spacer block 16 in the natural tension of the knee joint. Different tibial spacer paddles 10 can be provided with different thicknesses in order to allow a surgeon to trial the knee joint for different prosthetic devices at a desired level of tension.

Figure 4D:
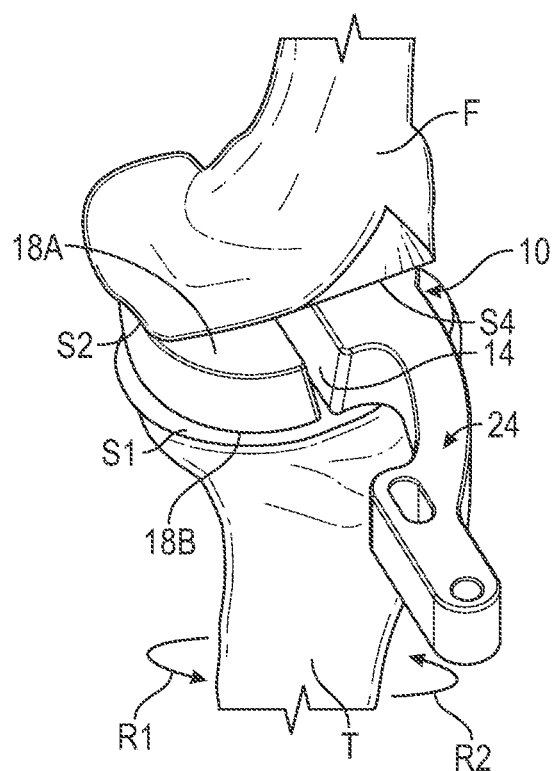
FIG. 4D is an anterior perspective view of the tibial spacer paddle of FIG. 4C illustrating natural rotation of the tibia.

FIG. 4D is an anterior perspective view of tibial spacer paddle 10 of FIG. 4C illustrating natural rotation of tibia T. As mentioned, with bearing surface 18A flushly engaged with distal surface S2 of femur F and bearing surface 18B flushly engaged with proximal surface S1 of tibia T, tibia T is free to rotate against spacer block 16, as shown by arrows of rotation R1 and R2. Resected surface S4 of femur F can allow access to indicator groove 14 for both visual inspection and insertion of a tool or instrument.

Figure 4E:
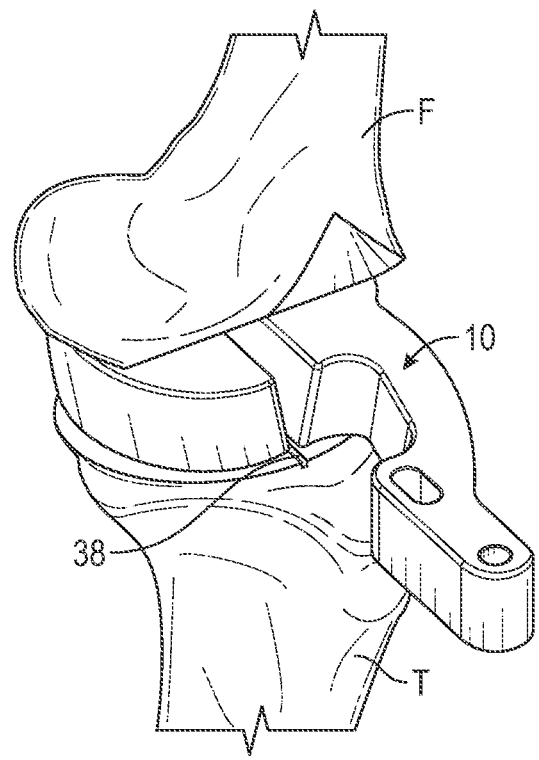
FIG. 4E is an anterior perspective view of the tibial spacer paddle of FIG. 4D with a marking of the resected tibial surface at the indicator groove.
Figure 4F:
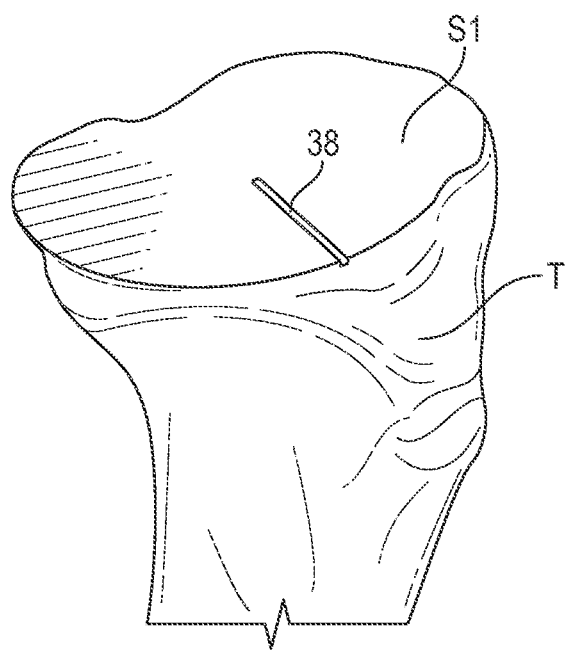
FIG. 4F is an anterior perspective view of the resected tibia of FIG. 4E showing the marked resected tibial surface.

FIG. 4E is an anterior perspective view of tibial spacer paddle 10 of FIG. 4D with marking 38 of the resected tibial surface at indicator groove 14. FIG. 4E is the same as FIG. 4D except for arrows of rotation R1 and R2 being removed and marking 38 being shown on proximal surface S1 within the bounds of indicator groove 14. FIG. 4F is an anterior perspective view of resected tibia T of FIG. 4E showing proximal surface S1 including marking 38. FIG. 4F shows tibia T in the same orientation as FIG. 4E but without tibial spacer paddle 10.

Indicator groove 14 can align with the center of femur F, e.g. the center position between the medial and lateral condyles that is coincident with femur axis AF. However, tibia T can be offset from the orientation of femur F such that the center of tibia T coincident with tibia axis AT is not aligned with the center of femur F. Tibial spacer paddle 10 includes indicator groove 14 to allow a surgeon to visualize and mark the center of femur F relative to the rotational position of tibia T in order to prepare tibia T and femur F for implantation of prosthetic knee joint devices. An instrument or tool, such as a pen, Bovie, marker, scalpel or pick, can be inserted into indicator groove 14 at bearing surface 18A and pushed through indicator groove 14 to penetrate beyond bearing surface 18B to contact proximal surface S1 of tibia T.

Marking 38, which can comprise a stripe of ink from a marker, a score in the surface of proximal surface S1 from a pick, or the like, can provide a fixed indicator on proximal surface S1 that points to where the center of femur F aligns on tibia T. As such, the center of a prosthetic tibial implant to be attached to proximal surface S1 of tibia T can be aligned with marking 38 upon implantation. Thus, for example, bearing surfaces of the prosthetic tibial implant configured to mate with condylar surfaces of a prosthetic femoral implant to be attached to femur F can be oriented so that tibia T will have the natural rotational orientation when in full extension. When properly aligned in extension, the prosthetic femoral and tibial components will not resist the natural orientation of the knee and joint pain and discomfort can be avoided.

Tibial spacer paddle 10 provides passive engagement with distal surface S2 of femur F. Tibial spacer paddle 10 is held in frictional engagement with femur F via feet 12A and 12B. Other embodiments of tibial spacer paddles can include features for providing positive engagement with femur F.

Using the above-described device and procedures, a method for determining rotation between a femur and a tibia can include the following steps: resect a femur and a tibia; position the tibia into approximately sixty degrees of flexion; insert a tibial spacer paddle into an anterior opening between resections of the tibia and femur; engage medial and lateral paddle feet with posterior surfaces of the femur so that the tibial spacer paddle is linked to the femur; extend the tibia into extension so the tibia rotates against the tibial spacer paddle; evaluate joint tension between the tibia and femur; insert tibial spacer paddles of different thicknesses into the anterior opening until a desired joint tension is achieved; making sure the medial and lateral paddle feet are engaged with posterior surface of femur, allow the tibia to rotate into a natural position against the tibial spacer paddle; identify a center of the femur at an indicator groove in the center of the tibial spacer paddle; and mark the center of the femur on the tibia using the indicator groove.

Figure 5:
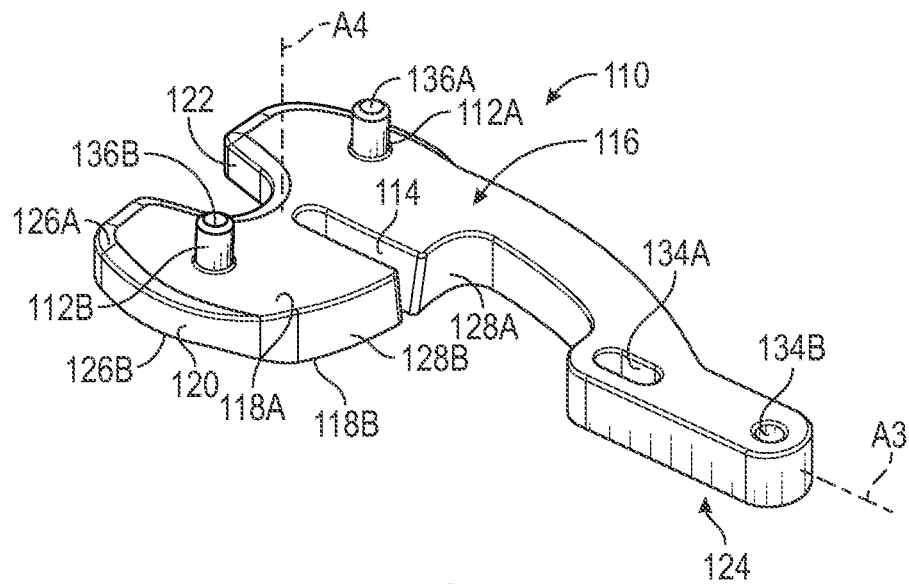
FIG. 5 is a perspective view of a tibial spacer paddle having alignment pegs and an indicator groove.
Figure 6:
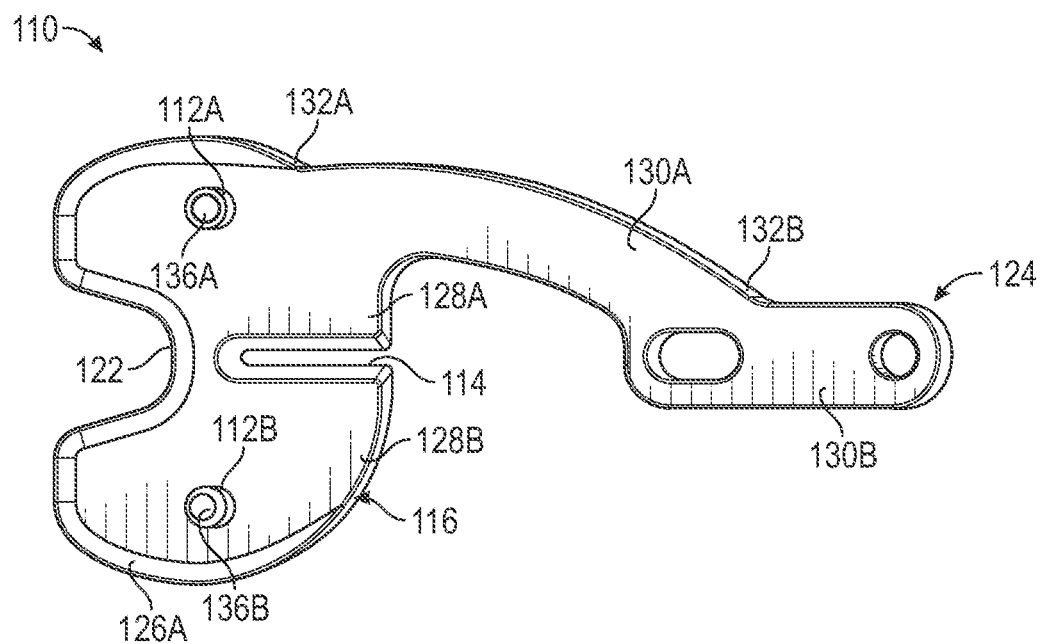
FIG. 6 is a top view of the tibial spacer paddle of FIG. 5 showing a location for the indicator groove.

FIG. 5 is a perspective view of tibial spacer paddle 110 having alignment pegs 112A and 112B and indicator groove 114 disposed in spacer block 116. FIG. 6 is a top view of tibial spacer paddle 110 of FIG. 5 showing a location for indicator groove 114 relative to bearing surface 118A. FIGS. 5 and 6 are discussed concurrently. Alignment pegs 112A and 112B can be configured to provide positive engagement with a femoral prosthetic component attached to femur F.

Spacer block 116 can include first bearing surface 118A, second bearing surface 118B, edge periphery surface 120, notch 122 and handle 124. Spacer block 116 can have a thickness between bearing surface 118A and bearing surface 118B that can differ in different embodiments in order to trial the tension in the knee joint. Spacer block 116 can generally be thinner than spacer block 16 due to spacer block 116 being configured to mate with femoral component 240. Edge periphery surface 120 can include edge chamfers 126A and 126B. Notch 122 and indicator groove 114 can extend into space block 116 to form first condylar portion 128A and second condylar portion 128B. Handle 124 can extend from edge periphery surface 120 of spacer block 116 and can include first segment 130A and second segment 130B. Second segment 130B can comprise an elongate body having a central axis A3 that is configured to extend axially in the direction of indicator groove 114.

Tibial spacer paddle 110 is configured similarly as tibial spacer paddle 10 of FIGS. 1-3 except feet 12A and 12B are replaced by alignment pegs 112A and 112B and chamfers 26A and 26B are replaced by edge chamfers 126A and 126B. Additionally, posterior surfaces 36A and 36B are replaced by proximal surfaces 136A and 136B. All other elements are numbered similarly as 100 series numbers.

Alignment pegs 112A and 112B can be configured to hold spacer block 116 into engagement with femoral implant 140 (FIG. 7) attached to a resected femur. Proximal surfaces 136A and 136B can protrude or project from first bearing surface 118A so that pegs 112A and 112B are perpendicular to bearing surface 118A. However, in other examples, superior surfaces 136A and 136B can extend at other angles relative to bearing surface 118A for use with different femoral implants than the one shown in FIG. 7. Thus, alignment pegs 112A and 112B can remain engaged with femoral component 140 as the knee joint is moved through flexion. If desired, a surgeon can grasp handle 124 to facilitate engagement of spacer block 116 and the femur. As the tibia moves from flexion to extension, the tibia can rotate against bearing surface 118B along vertical axis A4, as described in greater detail with reference to FIGS. 8A-8C.

Figure 7:
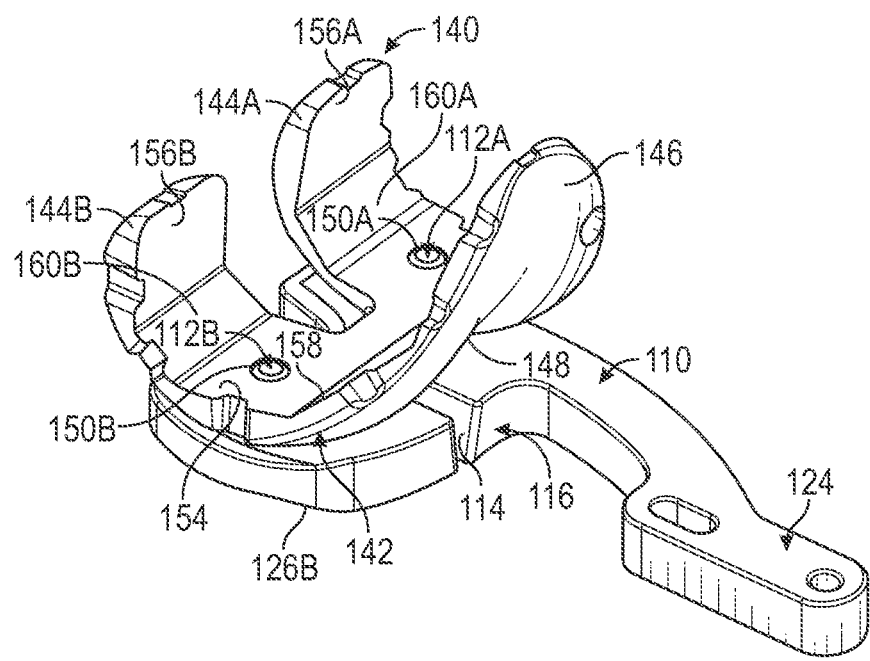
FIG. 7 is a perspective view of the tibial spacer paddle of FIG. 5 and a femoral component engaged with the alignment pegs.

FIG. 7 is a perspective view of tibial spacer paddle 110 of FIG. 5 and femoral component 140 engaged with alignment pegs 112A and 112B. Femoral component 140 can comprise a femoral trial component that has distal surfaces for engaging a tibial component and proximal surfaces for engaging a resected femur. A plurality of femoral components can be provided with each of the femoral components having different parameters, such as thicknesses, varus/valgus angles, etc., for trialing with the anatomy of a patient. Femoral component 140 can be held in place against femur F using bone cement, fasteners or by force fit with the resected surfaces.

Femoral component 140 can comprise tibia-facing surface 142 formed along the outer periphery of femoral component 140 and can include lateral condyle 144A and medial condyle 144B. Lateral condyle 144A and medial condyle 144B can be configured for articulation with a prosthetic tibial component. Femoral component 140 can include anterior flange 146 having trochlear groove 148. Trochlear groove 148 can extend from a generally anterior and proximal starting point to a generally posterior and distal terminus. Trochlear groove 148 can form an anterior articular surface of femoral component 140 for articulation with a natural or prosthetic patella.

Femoral component 140 can define a transverse plane that can be a plane tangent to distal-most points of lateral and medial condyles 144A and 144B. Femoral component 140 can also define a coronal plane that can be a plane tangent to the posterior-most points of the lateral and medial condyles 144A and 144B, when viewed from a lateral side of femoral component 140, can be perpendicular to the transverse plane.

Femoral component 140 can include peg ports 150A and 150B that can be configured to engage alignment pegs 112A and 112B, respectively. Peg ports 150A and 150B can be positioned in the transverse plane at the distal-most points of lateral and medial condyles 144A and 144B, respectively.

Femoral component 140 can comprise femur-contacting portion 152 formed along the inner periphery of femoral component 140 and can include distal surface 154, first posterior surface 156A, second posterior surface 156B, angled anterior surface 158, first quarter surface 160A and second quarter surface 160B. Distal surface 154, first posterior surface 156A, second posterior surface 156B, angled anterior surface 158, first quarter surface 160A and second quarter surface 160B can be configured to align and mate with distal surface S2, first posterior surface S3A, second posterior surface S3B, angled anterior surface S4, first quarter surface S5A and second quarter surface S5B, respectively, of tibia T in FIGS. 4A-4F.

Figure 8A:
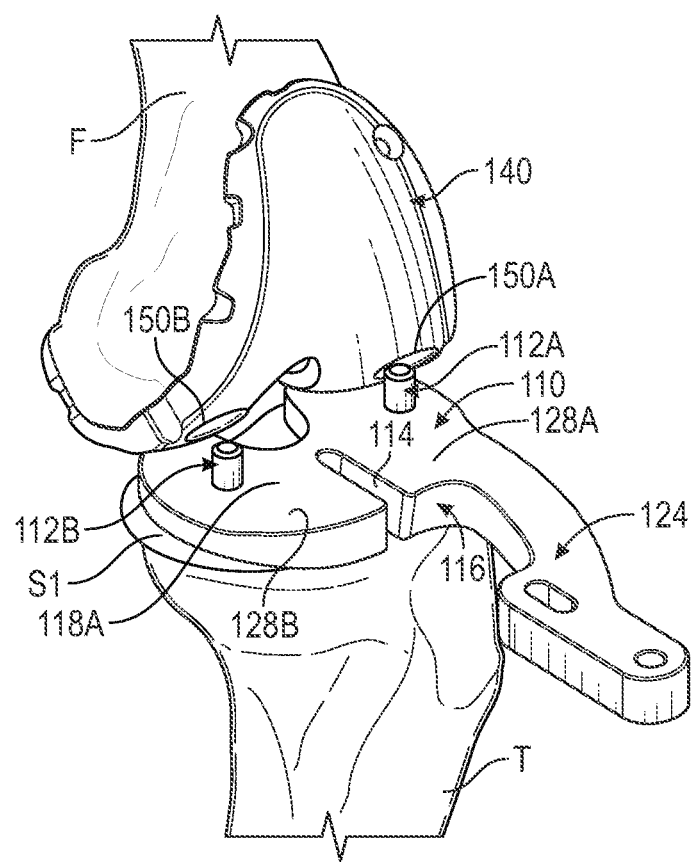
FIG. 8A is a perspective view of the femoral component of FIG. 7 attached to a resected femur and the tibial spacer paddle of FIG. 5 inserted between the femoral component and a resected tibia in approximately sixty degrees of flexion.

FIG. 8A is a perspective view of femoral component 140 of FIG. 7 attached to resected femur F and tibial spacer paddle 110 of FIG. 5 inserted between femoral component 140 and resected tibia T in approximately sixty degrees of flexion.

With the knee joint in flexion, tibial spacer paddle 110 can be inserted into an incision in an anterior portion of a knee joint so that handle 124 can extend out of the incision. Second bearing surface 118B can be positioned against resected proximal surface S1. Femur F and tibia T of the knee joint can be pushed or pulled apart, such as by using a retractor, to provide space for tibial spacer paddle 110. Edge chamfers 126A and 126B can facilitate insertion of tibial spacer paddle 110 by narrowing spacer block 116 and can eliminate sharp edges that could potentially interfere with or damage ligaments in the knee joint. Tibial spacer paddle 110 can be positioned so that alignment pegs 112A and 112B align with peg ports 150A and 150B, respectively, in femoral component 140.

Figure 8B:
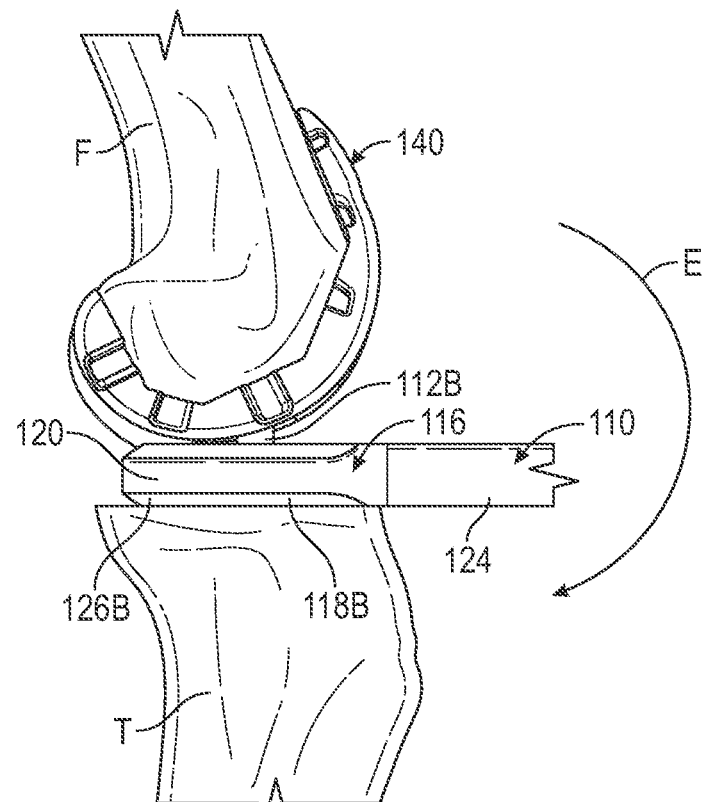
FIG. 8B is a side view of the femoral component and tibial spacer paddle of FIG. 8A being moved toward full extension so that the alignment pegs align with corresponding ports in the femoral component.

FIG. 8B is a side view of femoral component 140 and tibial spacer paddle 110 of FIG. 8A being moved toward full extension so that alignment pegs 112A and 112B align with and are inserted into corresponding peg ports 150A and 150B in femoral component 140. As tibia T moves into extension, indicated by arrow E, handle 124 can be used by a surgeon to guide alignment pegs 112A and 112B into peg ports 150A and 150B. As pegs 112A and 112B engage femoral component 140, proximal surface S1 of tibia T can slide against bearing surface 118B and tibia T undergoes natural rotation into extension.

Figure 8C:
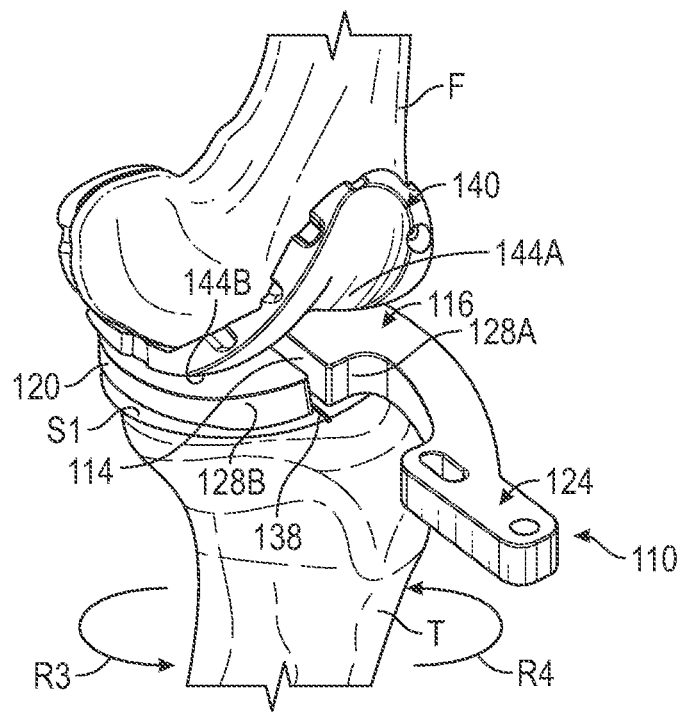
FIG. 8C is a perspective view of the femoral component and tibial spacer paddle of FIG. 8B in full extension with the tibia rotated into a natural alignment position so that a resected tibia surface can be marked at the indicator groove.

FIG. 8C is a perspective view of femoral component 140 and tibial spacer paddle 110 of FIG. 8B in full extension with tibia T rotated into a natural alignment position so that resected proximal surface S1 can be marked at the indicator groove 114. With bearing surface 118A flushly engaged with femoral component 140 and bearing surface 118B flushly engaged with proximal surface S1 of tibia T, tibia T is free to rotate against spacer block 116, as shown by arrows of rotation R3 and R4. Pegs 112A and 112B hold tibial spacer paddle 110 in positive engagement with femoral component 140 at peg ports 150A and 150B. This engagement can reduce or eliminate slippage of tibial spacer paddle 110 relative to femur F, which can help provide an accurate indication of the natural rotational position of tibia T relative to femur F when in extension. Indicator groove 114 can be visible between lateral and medial condyles 144A and 144B of femoral component 140 for both visual inspection and insertion of a tool or instrument.

Marking 138, which can comprise a stripe of ink from a marker, a score in the surface of proximal surface S1 from a pick, or the like, provides a fixed indicator on proximal surface S1 that points to where the center of femur F aligns on tibia T. As such, the center of a prosthetic tibial implant to be attached to proximal surface S1 of tibia T can be aligned with marking 138 upon implantation.

Using the above-described device and procedures, a method for determining rotation between a femur and a tibia can include the following steps: resect a femur and a tibia; position the tibia into approximately sixty degrees of flexion; attach a femoral component to the resected femur; insert a tibial spacer paddle into an anterior opening between resections of the tibia and femur; guide tibial spacer paddle pegs into corresponding ports in the femoral component to link the tibial spacer paddle and the femoral component; extend the tibia into extension so the tibia rotates against the tibial spacer paddle; evaluate joint tension between the tibia and femur; insert tibial spacer paddles of different thicknesses into the anterior opening until a desired joint tension is achieved; allow the tibia to rotate against the tibial spacer paddle into a natural position; identify a center of the femur at an indicator groove in the center of the tibial spacer paddle; and mark the center of the femur on the tibia using the indicator groove.

Figure 9A:
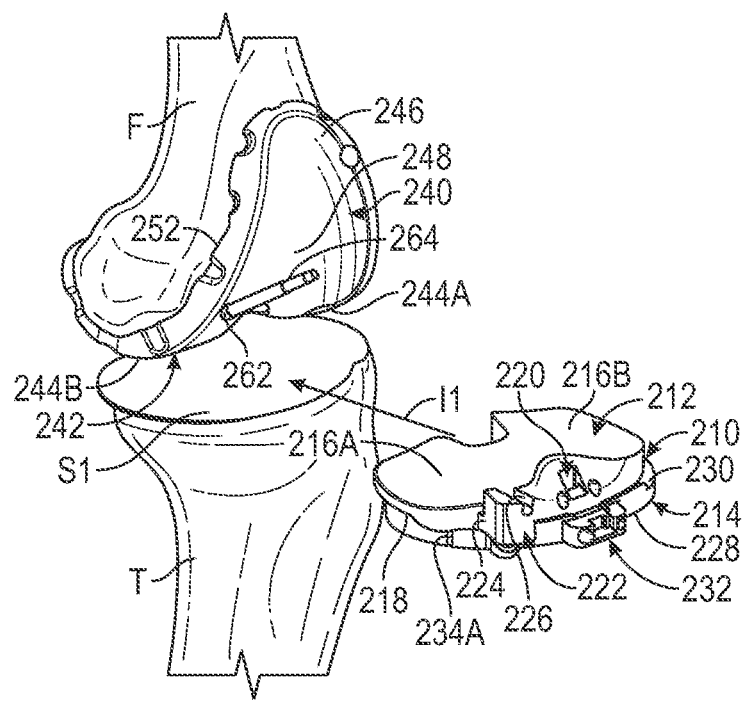
FIG. 9A is a perspective view of a femoral component attached to a resected femur and a tibial sizing system comprising a provisional component and a sizing plate aligned for insertion onto a resected tibia.

FIG. 9A is a perspective view of tibial sizing system 210 comprising provisional component 212 and sizing plate 214 aligned for insertion onto resected tibia T. Provisional component 212 can include condyle bearing surfaces (or articulating surfaces) 216A and 216B, an opposing engagement (bearing) surface 218, socket 220 and engagement tab 222. Engagement tab 222 can include body 224 and notch 226. Sizing plate 214 can comprise bone-facing (bone-engaging) surface 228, engagement surface 230, socket 232 and etch lines 234A and 234B. Sizing plate 214 is discussed further with reference to FIG. 9E. In examples, provisional component 212 can comprise a one-piece Tibial Articular Surface Provisional (TASP), commercially available from Zimmer Biomet under the Persona brand, modified to include engagement tab 222. In examples, sizing plate 214 can comprise a tibial sizing plate as described in U.S. Pat. No. 5,634,927 to Houston et al., which is assigned to Zimmer, Inc., modified to include etch lines 234A and 234B. U.S. Pat. No. 5,634,927 to Houston et al. is hereby incorporated by this reference in its entirety for all purposes.

FIG. 9A also shows femoral component 240 attached to resected femur F. Femoral component 240 can be similar to that of femoral component 140 of FIG. 7, except for the addition of pin port 262. All other elements are numbered similarly as 200 series numbers. For example, femoral component 240 can comprise tibia-facing surface 242 formed along the outer periphery of femoral component 240, which can include lateral condyle 244A and medial condyle 244B, anterior flange 246 having trochlear groove 248, and femur-contacting portion 252 formed along the inner periphery of femoral component 240, which can include distal surface 254, first posterior surface 256A, second posterior surface 256B, angled anterior surface 258, first quarter surface 260A and second quarter surface 260B.

Femoral component 240 can also include pin bore 262 for the reception of pin 264. Pin 264, such as a trocar pin, can be inserted into pin bore 262. Pin bore 262 can be positioned to align with engagement tab 222 when the centers of femoral component 240 and provisional component 212 are aligned.

Femoral component 240 can be attached to femur F in any suitable manner, as described above. Likewise, provisional component 212 can be attached to sizing plate 214 in a releasable manner. For example, provisional component 212 can be snap fit into sizing plate 214, as described below. Sizing plate 214 is configured to slide against proximal surface S1 of tibia T. Because femoral components 240 and tibial provisional component 214 can be configured as trialing components, femoral components 240 and provisional component 214 can be removably attached to the respective surfaces.

In FIG. 9A, tibia T and femur F can be resected to have surfaces as described with reference to FIG. 4A. Femoral component 240 can be attached to femur F and then tibial sizing system 210 can be inserted, as indicated by arrow I1, between femoral component 240 and resected proximal surface S1 of tibia T.

Figure 9B:
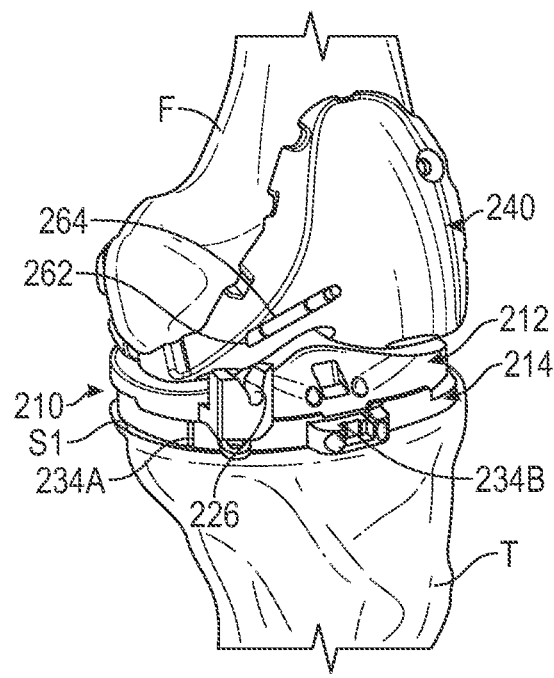
FIG. 9B is perspective view of the femoral component and the tibial sizing system of FIG. 9A with the tibial sizing system inserted between the femoral component and the resected tibia in extension.

FIG. 9B is perspective view of femoral component 240 and tibial sizing system 210 of FIG. 9A with tibial sizing system 210 inserted between femoral component 240 and resected tibia T in extension. As shown, both pin bore 262 and engagement tab 222 are positioned on the same side of femoral component 240 and tibial sizing system 210, respectively. As tibia T is moved into full extension, tibial sizing system 210 can be positioned so that notch 226 can align with pin 264, as proximal surface S1 of tibia T rotates against bone-facing surface 228 of sizing plate 214. With pin 2464 engaged with notch 226, provisional component 212 can be swapped out for provisional components of similar construction, but with different thicknesses. For example, the thickness between bearing surfaces 216A and 216B and engagement surface 218 can be different in different embodiments of sizing plates 214. The different thicknesses can be used to set the desired ligament tension between tibia T and femur F.

Figure 9C:
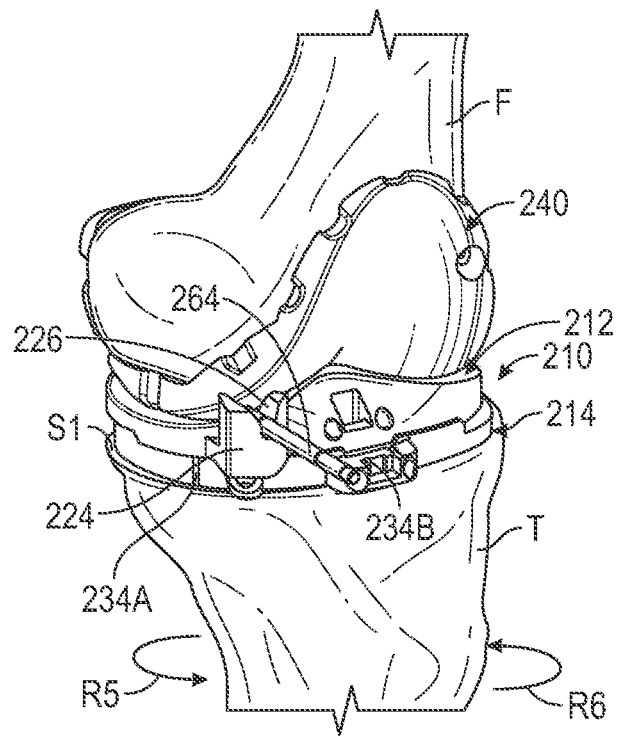
FIG. 9C is perspective view of the femoral component and the tibial sizing system of FIG. 9B with the femur in full extension and the tibia rotated so a pin extending into the femoral component aligns with a tab on the tibial provisional component.

FIG. 9C is perspective view of femoral component 240 and tibial sizing system 210 of FIG. 9B with femur F in full extension and tibia T rotated so pin 264 extending into femoral component 240 aligns with tab 222 on tibial provisional component 210. Once the desired tension is set, tibia T and femur F can be set into extension so that pin 264 aligns with notch 226. Tibia T can find a natural rotational position in extension with respect to femur F, as shown by arrows of rotation R5 and R6. For example, proximal surface S1 of tibia T can rotate against bone-facing surface 228 of sizing plate 214.

Figure 9D:
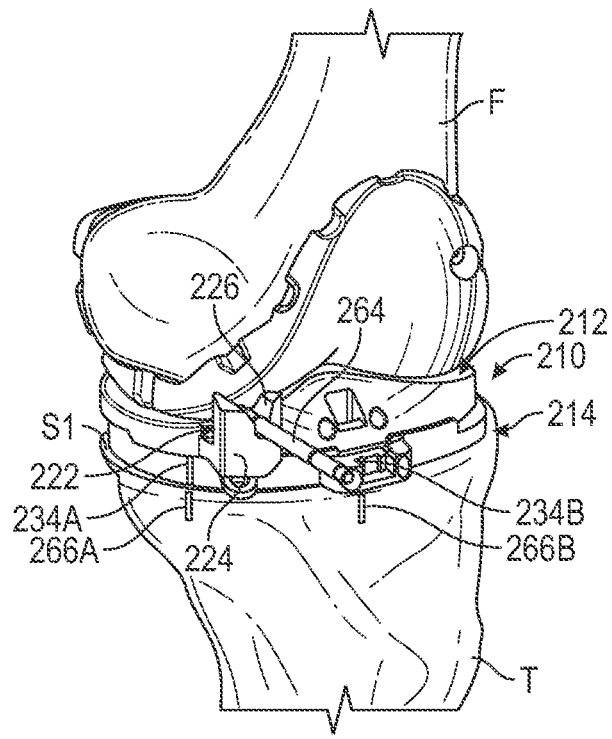
FIG. 9D is a perspective view of the femoral component and the tibial sizing system of FIG. 9B with the pin extending along the tab and alignment markings on the tibia.

FIG. 9D is a perspective view of femoral component 240 and tibial sizing system 210 of FIG. 9B with pin 264 extending along tab 222 and alignment markings 266A and 266B on the tibia T. Etch lines 234A and 234B can be positioned along tibia T adjacent proximal surface S1. Markings 266A and 266B, which can comprise a stripe of ink from a pen, a Bovie, a marker, a score in the surface of proximal surface S1 from a pick, or the like, provides a fixed indicator on proximal surface S1 that points to where the center of femur F and a secondary reference point align on tibia T. For example, marking 266B can indicate the center of femur F and marking 266A can be used to verify rotation of tibia T and provide a secondary reference point. As such, the center of a prosthetic tibial implant to be attached to proximal surface S1 of tibia T can be aligned with marking 266B upon implantation and a secondary mark corresponding to etch line 234B on the prosthetic tibial implant can be aligned with marking 266A.

Figure 9E:
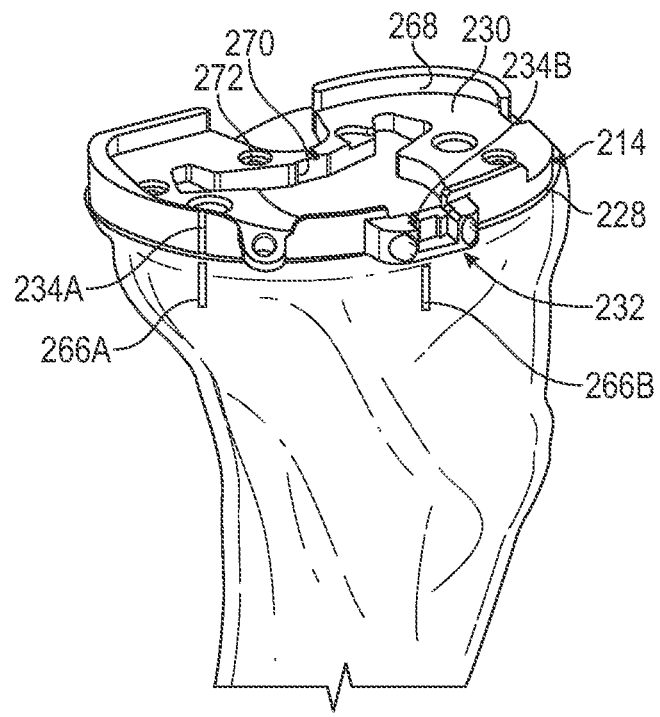
FIG. 9E is a perspective view of the resected tibia of FIG. 9D showing the sizing plate of the tibial sizing system disposed on the resected tibia surface.

FIG. 9E is a perspective view of resected tibia T of FIG. 9D showing sizing plate 214 of the tibial sizing system 210 disposed on the resected tibia surface T. Sizing plate 214 can include wall 268, keel socket 270 and fixation bores 272. Fixation bores 272 can comprise openings in engagement surface 230 into which fasteners can be inserted to retain sizing plate 214 against proximal surface S1 of tibia T. Keel socket 270 can comprise an opening in engagement surface 230 into which a fixation feature, such as a keel, of a prosthetic tibial component can be inserted. Wall 268 can comprise a flange extending from engagement surface 230 that can function to retain provisional component 212. For example, provisional component 212 can include corresponding features (e.g., cutback 290 and cutback 292 of FIG. 14) that allow provisional component 212 to be snap fit into wall 268. Etch lines 234A and 234B and markings 266A and 266B can be used to orient keel socket 270 relative to proximal surface S1 to provide rotational orientation of the prosthetic tibial component relative to the mechanical axis (e.g., vertical axis A2 of FIG. 1 or tibial axis AT of FIG. 4A) of tibia T. Further description of sizing plate 214 can be found in the aforementioned '927 patent to Houston et al.

Using the above-described device and procedures, a method for determining rotation between a femur and a tibia can include the following steps: resect a femur and a tibia; position the tibia into approximately sixty degrees of flexion; attach a femoral component to the resected femur; insert a pin into the femoral component; connect a tibial sizing plate to tibial provisional component; insert the connected tibial sizing plate and tibial provisional component into an anterior opening between resections of the tibia and femur; extend the tibia into extension so the tibia rotates against the tibial sizing plate; guide the pin into a notch in the tibial provisional component to link the tibial provisional component and the femoral component; evaluate joint tension between the tibia and femur; connect tibial provisional components of different thicknesses to the tibial sizing plate until a desired joint tension is achieved; allow the tibia to rotate against the tibial sizing plate into a natural position; identify a center of the femur at an indicator in the center of the tibial sizing plate; and mark the center of the femur on the tibia using the indicator.

Figure 10:
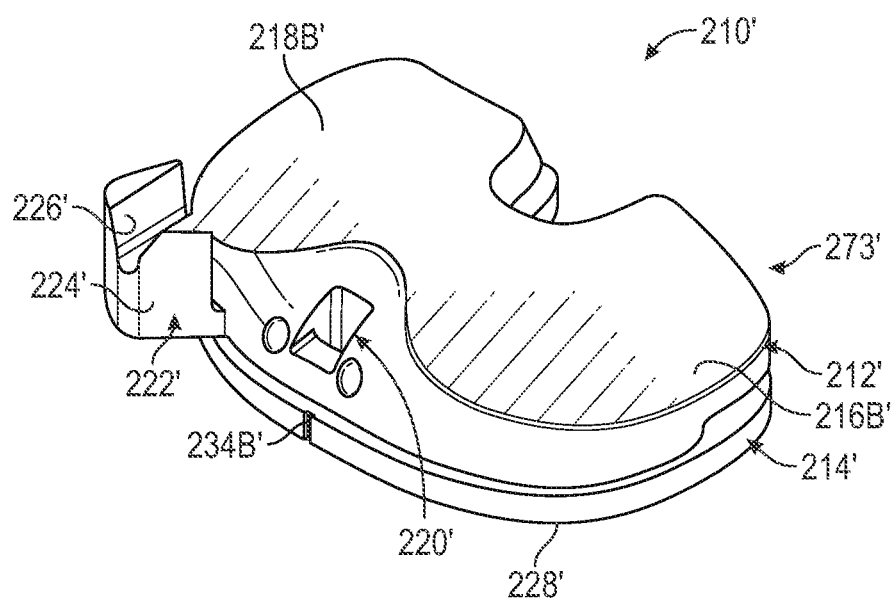
FIG. 10 is a perspective view of another embodiment of the tibial sizing system of FIG. 9A wherein the provisional component and sizing plate are integrated into a monolithic component.

FIG. 10 is a perspective view of another embodiment of tibial sizing system 210' of FIG. 9A wherein provisional component 212' and sizing plate 214' are integrated into monolithic component 273. Monolithic component 273 can function the same as the combination of provisional component 212 and sizing plate 214, except for being a single, unitary component. Thus, a plurality of monolithic components 273 can be provided with different thicknesses in order to trial the desired ligament tension between tibia T and femur F. Certain features can be eliminated from tibial sizing system 210' for simplicity, such as socket 232. Additionally, engagement surface 218 and engagement surface 230 can be eliminated because monolithic component 273 is fused along this planar intersection as compared to tibial sizing system 210.

Using the above-described device and procedures, a method for determining rotation between a femur and a tibia can include the following steps: resect a femur and a tibia; position the tibia into approximately sixty degrees of flexion; attach a femoral component to the resected femur; insert a pin into the femoral component; insert a tibial provisional component into an anterior opening between resections of the tibia and femur; extend the tibia into extension so the tibia rotates against the tibial provisional component; guide the pin into a notch in the tibial provisional component to link the tibial provisional component and the femoral component; evaluate joint tension between the tibia and femur; insert tibial provisional components of different thicknesses into the anterior opening until a desired joint tension is achieved; allow the tibia to rotate against the tibial provisional component into a natural position; identify a center of the femur at an indicator in the center of the tibial provisional component; and mark the center of the femur on the tibia using the indicator.

Figure 11:
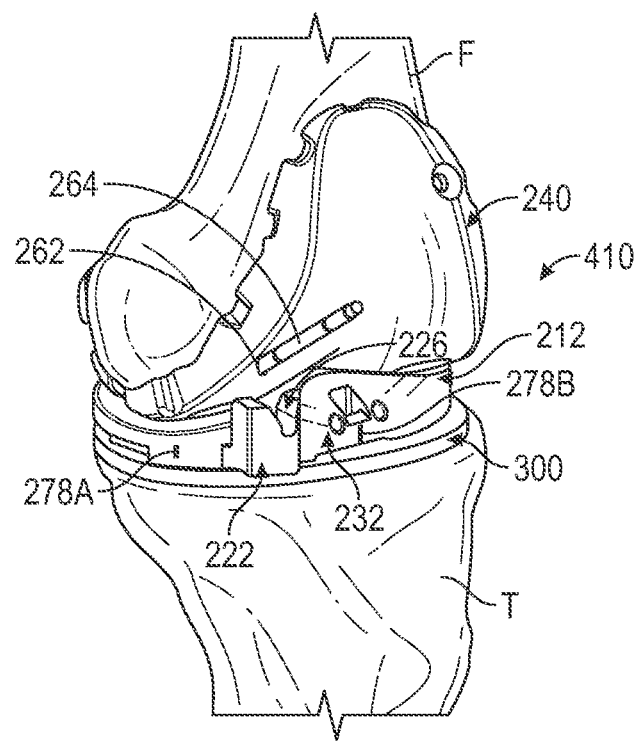
FIG. 11 is a perspective view of a femoral component attached to a resected femur and a tibial sizing system comprising a provisional component and a tibial plate with a pivot mount inserted between the femoral component and a resected tibia.

FIG. 11 is a perspective view of femoral component 240 attached to resected femur F and tibial sizing system 410 comprising provisional component 212 and tibial plate 300 with pivot mount 302 (FIG. 12) inserted between femoral component 240 and resected tibia T. Provisional component 212 can include pivot port 274 (FIG. 14) that can receive pivot mount 302 such that provisional component 212 can rotate or pivot relative to tibial plate 300.

Femur F and tibia T can be resected as described herein. Femoral component 240 can be configured the same as femoral component 240 of FIGS. 9A-9D to include pin bore 262 for the reception of pin 264. Provisional component 212 can be similar to that of provisional component 212 of FIGS. 9A-9D, except for the addition of pivot port 274 and etch lines 278A and 278B. All other elements are numbered the same.

As mentioned, pivot port 274 and pivot mount 302 can connect in a rotational engagement. Tibial plate 300 can engage tibia T in a free manner and provisional component 212 can slide against tibial plate 300 to facilitate determination of the natural rotation of tibia T.

Figure 12:
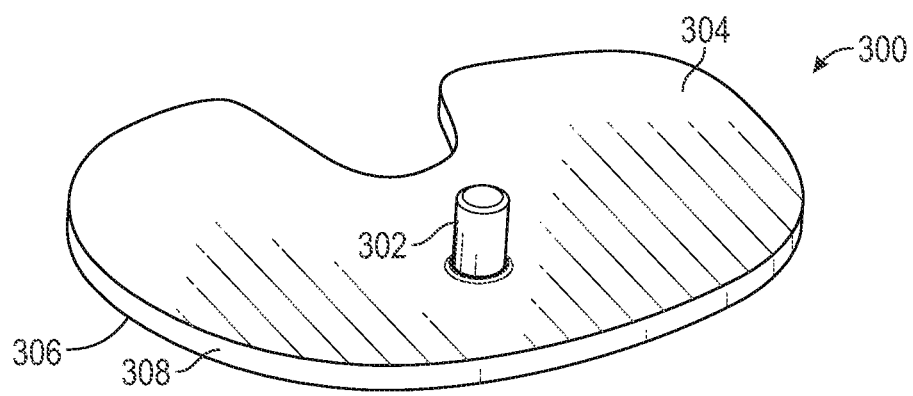
FIG. 12 is a perspective view of the tibial plate of FIG. 11 showing the pivot mount comprising a peg.

FIG. 12 is a perspective view of tibial plate 300 with pivot mount 302 of FIG. 11 that can be configured to extend from bearing surface 304. Additionally, tibial plate 300 can include bone-facing (bone-engaging) surface 306 and edge periphery region 308, which can connect bearing surface 304 and bone-facing surface 306. Pivot mount 302 can comprise a cylindrical peg extending perpendicularly from bearing surface 304. Bearing surface 304 can have a smooth finish to reduce frictional engagement with engagement surface 218. For example, tibial plate 300 can be finished, such as via a polishing operation, to reduce the coefficient of friction of bearing surface 304.

Figure 13:
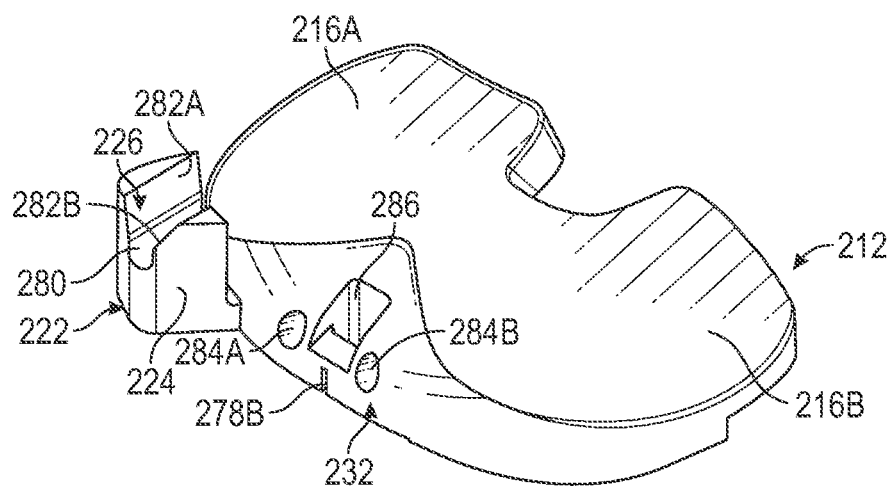
FIG. 13 is a top perspective view of the provisional component of FIG. 11 showing an engagement tab.

FIG. 13 is a top perspective view of provisional component 212 of FIG. 11 showing the construction of engagement tab 222 and socket 232. Engagement tab 222 can include body 224 and notch 226. Socket 232 can include bores 284A and 284B and through-port 286.

Notch 222 can include bottom portion 280 and sidewalls 282A and 282B. Notch 222 can be configured to receive a pin, rod or other member extending form femoral component 240, such as pin 264. For example, bottom portion 280 can form a semi-circular wall. Pin 264 can be cylindrical and bottom portion 280 can be configured to have a matching diameter to flushly receive pin 264. Sidewalls 282A and 282B can extend from bottom portion 280 upward away from the remainder of body 224 and the distance between sidewalls 282A and 282B can increase as sidewalls 282A and 282B extend further away from bottom portion 280. In other words, portions of body 224 forming sidewalls 282A and 282B can taper as sidewalls 282A and 282B extend away from bottom portion 280. As such, the wider portion of notch 222 in the proximal direction can guide pin 264 into engagement with bottom portion 280 as tibia T is moved into full extension.

Socket 232 can be configured to receive a tool to facilitate insertion and removal of provisional component 212. In examples, bores 284A and 284B can be configured to receive pins of a tibial insertion handle. Through-port 286 can thereafter be configured to receive a tooth of a spring-loaded slide on the handle that locks the handle to provisional component 212. In examples, socket 232 can be configured to operate with the pins and the tooth described in U.S. Pat. No. 8,603,101 to Claypool et al., which is hereby incorporated by this reference in its entirety for all purposes.

Figure 14:
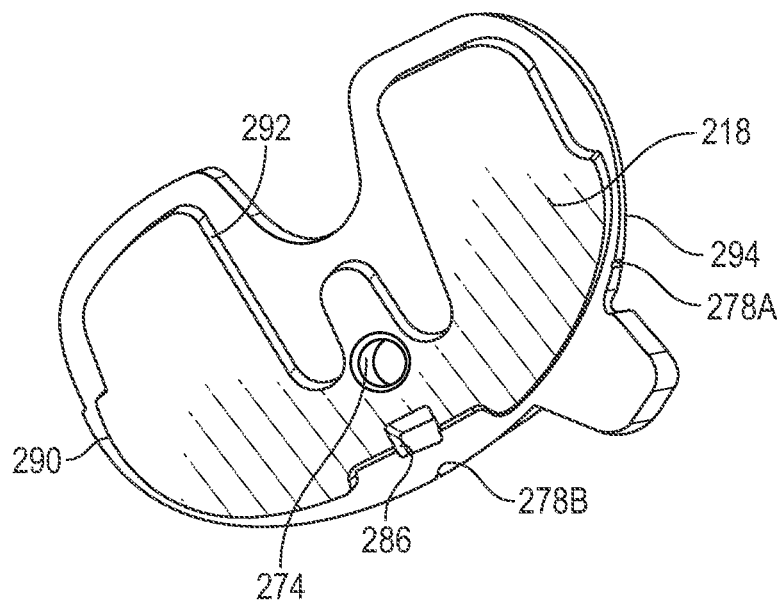
FIG. 14 is a bottom perspective view of the provisional component of FIG. 11 showing cut-backs of an engagement surface.

FIG. 14 is a bottom perspective view of provisional component 212 of FIG. 11 showing engagement surface 218, pivot port 274, anterior cutback 290 and posterior cutback 292. Engagement surface (or bearing surface) 218 can be smooth to slide against bearing surface 304. Pivot port 274 can be located in engagement surface 218 and can be positioned to align with pivot mount 302. Pivot port 274 can comprise a cylindrical bore to receive pivot mount 302. Anterior cutback 290 and posterior cutback 292 can be recesses into engagement surface 218 that extend all the way to edge periphery surface 294. Edge periphery surface 294 can connect engagement surface 218 and condyle bearing surfaces 216A and 216B. Edge periphery surface 294 can also include etch lines 278A and 278B. Anterior cutback 290 and posterior cutback 292 can be configured to engage wall 268 of sizing plate 214 (FIG. 9E) to assist in retaining provisional component 212 in engagement with sizing plate 214. Additionally, anterior cutback 290 and posterior cutback 292 can allow engagement surface 218 to sit down into wall 268.

Figure 15A:
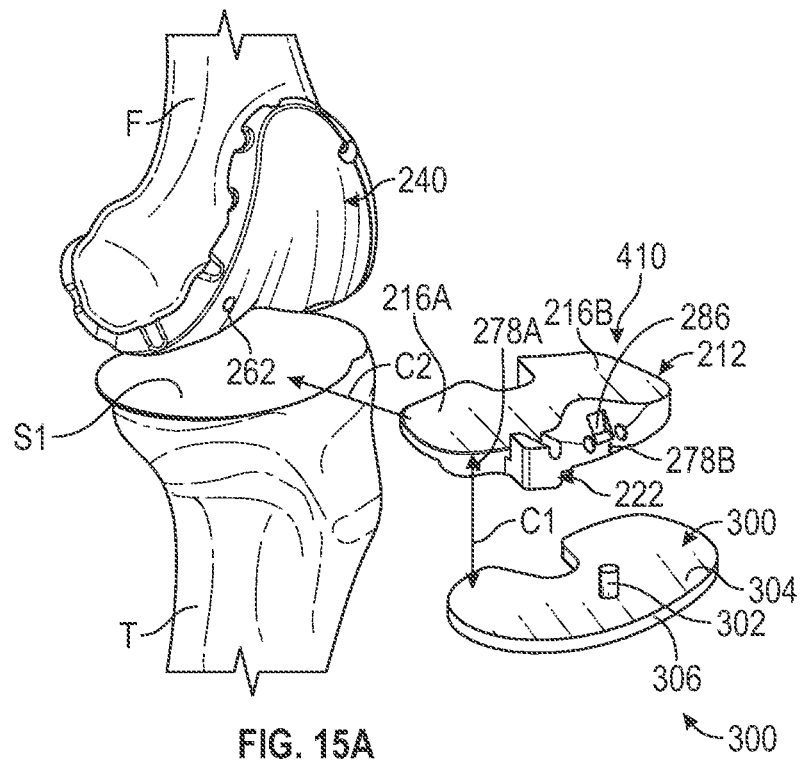
FIG. 15A is a perspective view of the femoral component of FIG. 11 attached to the resected femur and the tibial sizing system exploded from the resected tibia.

FIG. 15A is a perspective view of femoral component 240 of FIG. 11 attached to resected femur F and tibial sizing system 410 exploded from resected tibia T. As shown by arrow C1, tibial plate 300 can be connected to provisional component 212 by inserting pivot mount 302 into pivot port 274 (FIG. 14) to form assembled tibial sizing system 410. A biocompatible lubricant can be positioned between tibial plate 300 and provisional component 212 to facilitate relative rotation therebetween. As shown by arrow C2, the assembled tibial sizing system 210 can be inserted into a knee joint between tibia T and femur F so that surface 306 faces proximal surface S1 of tibia T. As such, bearing surfaces 216A and 216B can face toward femoral component 240. Different provisional components 212 of different thicknesses can be trialed between tibia T and femur F to find the proper tension.

Figure 15B:
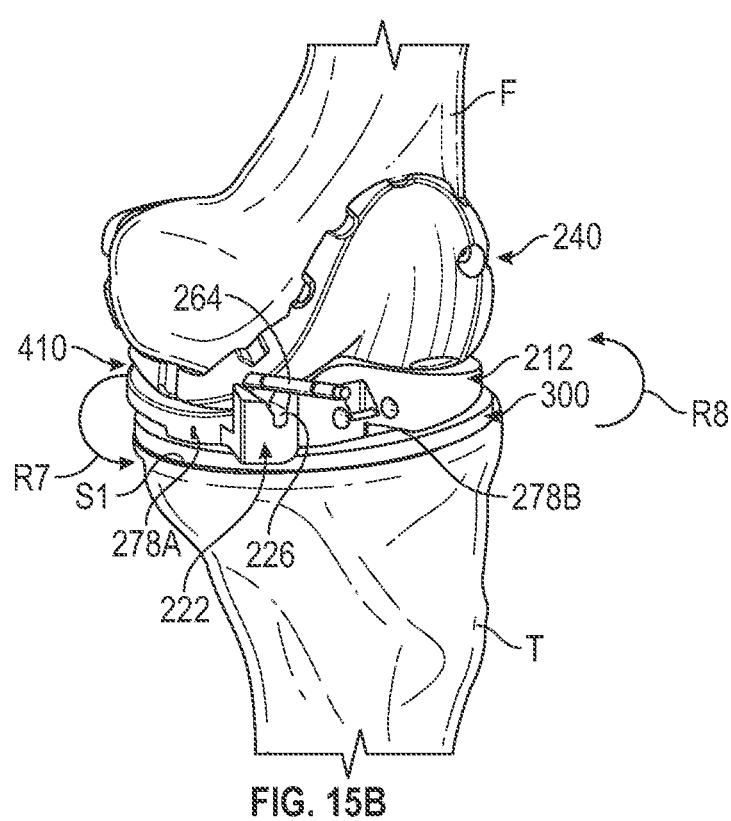
FIG. 15B is a perspective view of an assembled tibial sizing system of FIG. 15A inserted between the femoral component and the resected tibia with the tibia rotating into natural alignment so that a pin extending from the femoral component aligns with a tab on the provisional component.

FIG. 15B is a perspective view of assembled tibial sizing system 410 of FIG. 15A inserted between femoral component 240 and resected tibia T. Pin 264 can be inserted into pin bore 262 in femoral component 240. With pin 264 engaged with engagement tab 222 to lock relative rotation between femoral component 240 and provisional component 212, tibia T can rotate into natural alignment, as shown by arrows of rotation R7 and R8, as proximal surface S1 rotates against surface 306. Attachment of tibial plate 300 to provisional component 212 via pivot mount 302 allows tibial plate 300 to rotate with tibia T while sliding against proximal surface S1 to provide a better indication of the natural rotational position of tibia T relative to femur F when in extension. For example, tibia T can be less encumbered by resistance from tibial sizing system 410 to facilitate true rotation of tibia T.

Figure 15C:
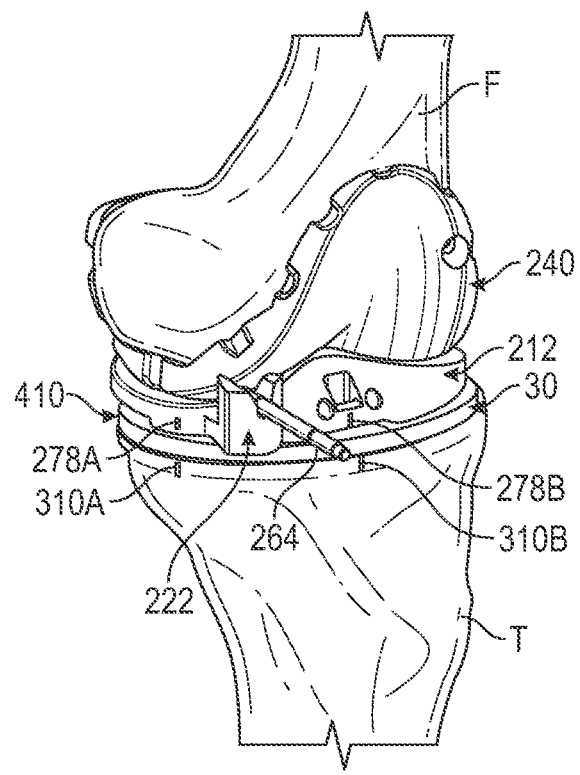
FIG. 15C is a perspective view of the tibia of FIG. 15B in full extension so that the pin is fully seated in the tab and the resected tibia is marked with alignment markings.

FIG. 15C is a perspective view of tibia T of FIG. 15B in full extension so that pin 264 is fully seated in engagement tab 222 and resected tibia T is marked with alignment markings 310A and 310B. As with markings 266A and 266B, markings 310A and 310B can provide reference marks for aligning with features of a prosthetic tibial component that provide rotational alignment of the prosthetic tibial component so that the prosthetic tibial component will not stress the knee joint when in extension, e.g., tibia T will find its natural rotational position without pushback from the prosthetic tibial component against a prosthetic femoral component. In various examples, tibial plate 300 can include cut-outs or windows (not shown) that permit proximal surface S1 to be viewed through tibial plate 300.

Using the above-described device and procedures, a method for determining rotation between a femur and a tibia can include the following steps: resect a femur and a tibia; position the tibia into approximately sixty degrees of flexion; attach a femoral component to the resected femur; insert a pin into the femoral component; connect a tibial plate to tibial provisional component at a pivot coupling; insert the coupled tibial plate and tibial provisional component into an anterior opening between resections of the tibia and femur; extend the tibia into extension so the tibia rotates against the tibial plate; guide the pin into a notch in the tibial provisional component to link the tibial provisional component and the femoral component; evaluate joint tension between the tibia and femur; connect tibial provisional components of different thicknesses to the tibial plate until a desired joint tension is achieved; allow the tibia to rotate against the tibial plate into a natural position while the tibial plate rotates against the tibial provisional component; identify a center of the femur at an indicator in the center of the tibial provisional component; and mark the center of the femur on the tibia using the indicator.

Figure 16:
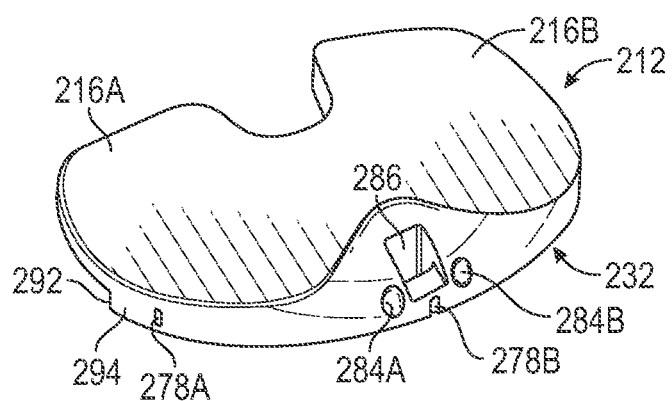
FIG. 16 is a top perspective view of another embodiment of the provisional component of FIGS. 13 and 14 without an alignment tab.
Figure 17:
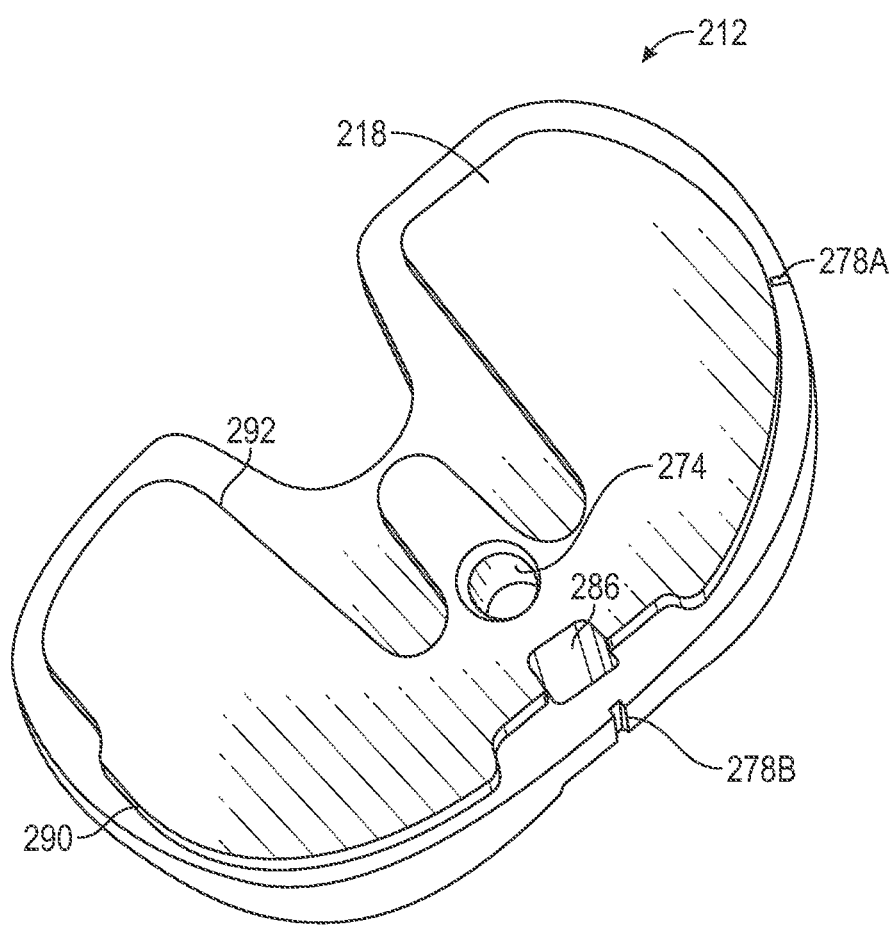
FIG. 17 is a bottom perspective view of the embodiment of the provisional component of FIG. 16 without the alignment tab.

FIG. 16 is a top perspective view of another embodiment of provisional component 212 of FIGS. 13 and 14, but without alignment tab 222. FIG. 17 is a bottom perspective view of the embodiment of provisional component 212 of FIG. 16. Alignment tab 222 can be omitted to simplify the construction of provisional component 212 and to simplify the method of trialing the tibial component. In some circumstances, it may be sufficient to determine the natural rotational position of tibia T without preventing relative rotation between femoral component 240 and provisional component 212. For example, the frictional engagement between lateral condyle 244A and medial condyle 244B with bearing surface 216A and bearing surface 216B, respectively, may be sufficient to immobilize provisional component 212. In examples, bearing surfaces 216A and 216B can be provided with texturing, such as knurling, pyramids, spikes or other projections to facilitate linked rotation.

Using the above-described device and procedures, a method for determining rotation between a femur and a tibia can include the following steps: resect a femur and a tibia; position the tibia into approximately sixty degrees of flexion; attach a femoral component to the resected femur; connect a tibial plate to tibial provisional component at a pivot coupling; insert the coupled tibial plate and tibial provisional component into an anterior opening between resections of the tibia and femur; extend the tibia into extension so the tibia rotates against the tibial plate; evaluate joint tension between the tibia and femur; connect tibial provisional components of different thicknesses to the tibial plate until a desired joint tension is achieved; allow the tibia to rotate against the tibial plate into a natural position while the tibial plate rotates against the tibial provisional component; identify a center of the femur at an indicator in the center of the tibial provisional component; and mark the center of the femur on the tibia using the indicator.

VARIOUS NOTES & EXAMPLES

Example 1 can include or use subject matter such as a tibial spacer paddle that can comprise: a spacer block that can comprise: a first bearing surface, a second bearing surface disposed opposite the first bearing surface, and an edge periphery region connecting the first bearing surface and the second bearing surface; a first foot extending from the first bearing surface at the edge periphery region; a second foot extending from the first bearing surface at the edge periphery region spaced from the first foot; a first alignment chamfer extending into the edge periphery region and the second bearing surface opposite the first foot; a second alignment chamfer extending into the edge periphery region and the second bearing surface opposite the second foot; an alignment slot extending into the edge periphery region opposite the first and second feet; and a handle extending from the spacer block.

Example 2 can include, or can optionally be combined with the subject matter of Example 1, to optionally include an alignment slot that can be positioned between the first and second feet.

Example 3 can include, or can optionally be combined with the subject matter of one or any combination of Examples 1 or 2 to optionally include a notch extending into the edge periphery region between the first and second alignment chamfers.

Example 4 can include, or can optionally be combined with the subject matter of one or any combination of Examples 1 through 3 to optionally include a notch that can align with the alignment slot on opposite sides of the spacer block.

Example 5 can include, or can optionally be combined with the subject matter of one or any combination of Examples 1 through 4 to optionally include a notch and an alignment slot that can separate the first bearing surface into first and second condylar surfaces.

Example 6 can include, or can optionally be combined with the subject matter of one or any combination of Examples 1 through 5 to optionally include first and second alignment chamfers that can be disposed at approximately forty-five degrees to the first and second bearing surfaces.

Example 7 can include, or can optionally be combined with the subject matter of one or any combination of Examples 1 through 6 to optionally include an alignment slot that can be tapered between the first bearing surface and the second bearing surface.

Example 8 can include, or can optionally be combined with the subject matter of one or any combination of Examples 1 through 7 to optionally include a handle that can extend from the edge periphery region proximate the alignment slot.

Example 9 can include, or can optionally be combined with the subject matter of one or any combination of Examples 1 through 8 to optionally include a handle that can comprise: a curved segment extending from the edge periphery region; and a straight segment connected to the curved segment.

Example 10 can include, or can optionally be combined with the subject matter of one or any combination of Examples 1 through 11 to optionally include a curved segment that can position the straight segment to align with the alignment slot.

Example 11 can include or use subject matter such as a tibial spacer system that can comprise: a spacer block that can comprise: a first bearing surface, a second bearing surface disposed opposite the first bearing surface, and an edge periphery region connecting the first bearing surface and the second bearing surface; a first peg extending from the first bearing surface; a second peg extending from the first bearing surface spaced from the first peg; an alignment slot extending into the edge periphery region; and a handle extending from the spacer block.

Example 12 can include, or can optionally be combined with the subject matter of Example 11, to optionally include an alignment slot that can be positioned between the first and second pegs.

Example 13 can include, or can optionally be combined with the subject matter of one or any combination of Examples 11 or 12 to optionally include a notch extending into the edge periphery region between the first and second pegs.

Example 14 can include, or can optionally be combined with the subject matter of one or any combination of Examples 11 through 13 to optionally include a notch that can align with the alignment slot on opposite sides of the spacer block.

Example 15 can include, or can optionally be combined with the subject matter of one or any combination of Examples 11 through 14 to optionally include a notch and an alignment slot that can separate the first bearing surface into first and second condylar surfaces.

Example 16 can include, or can optionally be combined with the subject matter of one or any combination of Examples 11 through 15 to optionally include a first peg and the a second peg that can be spaced from the edge periphery region.

Example 17 can include, or can optionally be combined with the subject matter of one or any combination of Examples 11 through 16 to optionally include an alignment slot that can be tapered between the first bearing surface and the second bearing surface.

Example 18 can include, or can optionally be combined with the subject matter of one or any combination of Examples 11 through 17 to optionally include a handle that can extend from the edge periphery region proximate the alignment slot.

Example 19 can include, or can optionally be combined with the subject matter of one or any combination of Examples 11 through 18 to optionally include a handle that can comprise: a curved segment extending from the edge periphery region; and a straight segment connected to the curved segment; wherein the curved segment positions the straight segment to align with the alignment slot.

Example 20 can include, or can optionally be combined with the subject matter of one or any combination of Examples 11 through 19 to optionally include a femoral component that can comprise: a first condylar body; a second condylar body connected to the first condylar body; a first alignment port located in the first condylar body and configured to align with the first peg; and a second alignment port located in the second condylar body and configured to align with the second peg.

Example 21 can include or use subject matter such as a tibial spacer system that can comprise: a provisional component that can comprise: a body, an articulating surface positioned on the body configured to engage condylar surfaces of a femoral component, and an alignment tab extending from the body; and a sizing extension extending from the body opposite the articulating surface, the sizing extension can comprise: a bone engagement surface, an edge periphery region extending from the bone engagement surface, and a first alignment indicator located on the edge periphery region of the sizing extension.

Example 22 can include, or can optionally be combined with the subject matter of Example 21, to optionally include a femoral component, the femoral component can comprise: a first condylar body; a second condylar body connected to the first condylar body; and a pin port extending into the femoral component, the pin port configured to align with the alignment tab.

Example 23 can include, or can optionally be combined with the subject matter of one or any combination of Examples 21 or 22 to optionally include a pin configured to be inserted into the pin port.

Example 24 can include, or can optionally be combined with the subject matter of one or any combination of Examples 21 through 23 to optionally include an alignment tab that can include a notch configured to receive the pin when the femoral component is located in an extension position relative to the articulating surface.

Example 25 can include, or can optionally be combined with the subject matter of one or any combination of Examples 21 through 24 to optionally include a body of the provisional component and the sizing extension can be integrated into a monolithic component.

Example 26 can include, or can optionally be combined with the subject matter of one or any combination of Examples 21 through 25 to optionally include a sizing extension that can comprise a plate attachable to the body of the provisional component. Example 27 can include, or can optionally be combined with the subject matter of one or any combination of Examples 21 through 26 to optionally include a plurality of provisional components, wherein each of the plurality of provisional components includes a different thickness.

Example 28 can include, or can optionally be combined with the subject matter of one or any combination of Examples 21 through 27 to optionally include a second alignment indicator located on the edge periphery region of the sizing extension; wherein the first alignment indicator is located proximate a center of a posterior portion of the edge periphery region and the second alignment indicator is spaced from the first alignment indicator.

Example 29 can include or use subject matter such as a tibial spacer system that can comprise: a provisional component that can comprise: an articulating surface configured to engage condylar surfaces of a femoral component, a first bearing surface disposed opposite the articulating surface, and a first edge periphery region connecting the articulating surface and the first bearing surface; a trial bearing that can comprise: a bone engagement surface, a second bearing surface disposed opposite the bone engagement surface, and a second edge periphery region connecting the bone engagement surface and the second bearing surface; and a pivot coupling connecting the first bearing surface and the second bearing surface configured to permit the trial bearing to rotate relative to the provisional component.

Example 30 can include, or can optionally be combined with the subject matter of Example 29, to optionally include a pivot coupling that can comprise: a peg extending from the second bearing surface; and a socket extending into the first bearing surface; wherein the peg is positioned to align with the socket when the second edge periphery region is substantially aligned with the first edge periphery region.

Example 31 can include, or can optionally be combined with the subject matter of one or any combination of Examples 29 or 30 to optionally include a peg that is positioned on the second bearing surface so as to be co-axial with a mechanical axis of the tibia; and a socket that is positioned on the first bearing surface so as to be co-axial with the mechanical axis of the tibia.

Example 32 can include, or can optionally be combined with the subject matter of one or any combination of Examples 29 through 31 to optionally include a provisional component that can further comprise an alignment tab extending from the first edge periphery region.

Example 33 can include, or can optionally be combined with the subject matter of one or any combination of Examples 29 through 32 to optionally include a femoral component, the femoral component can comprise: a first condylar body; a second condylar body connected to the first condylar body; and a pin port extending into the femoral component, the pin port configured to align with the alignment tab.

Example 34 can include, or can optionally be combined with the subject matter of one or any combination of Examples 29 through 33 to optionally include a pin configured to be inserted into the pin port.

Example 35 can include, or can optionally be combined with the subject matter of one or any combination of Examples 29 through 34 to optionally include a tab that can include a notch configured to receive the pin when the femoral component is located in an extension position relative to the articulating surface.

Example 36 can include, or can optionally be combined with the subject matter of one or any combination of Examples 29 through 35 to optionally include a first edge periphery region that can include a first alignment indicator.

Example 37 can include, or can optionally be combined with the subject matter of one or any combination of Examples 29 through 36 to optionally include a second alignment indicator located on the first edge periphery region of the provisional component; wherein the first alignment indicator is located proximate a center of a posterior portion of the first edge periphery region and the second alignment indicator is spaced from the first alignment indicator.

Example 38 can include, or can optionally be combined with the subject matter of one or any combination of Examples 29 through 37 to optionally include a plurality of provisional components, wherein each of the plurality of provisional components includes a different thickness.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method for determining rotation between a femur and a tibia in a knee joint, the method comprising:
    resecting a femur to produce a resected femoral surface;
    resecting a tibia to produce a resected tibial surface;
    positioning the tibia into flexion;
    attaching a femoral component to the resected femoral surface;
    inserting a pin into the femoral component;
    inserting a tibial component into an anterior opening between resections of the tibia and femur;
    extending the tibia into extension so the tibia rotates against the tibial component;
    locking the pin in engagement with the tibial component to link the tibial component and the femoral component;
    allowing the tibia to rotate against the tibial component into a natural position;
    identifying a location of the femur at an indicator on the tibial component; and
    marking the location of the femur on the tibia using the indicator.

2. The method of claim 1, wherein positioning the tibia into flexion comprises positioning the tibia into approximately sixty degrees of flexion.

3. The method of claim 1, wherein locking the pin in engagement with the tibial component to link the tibial component and the femoral component comprises:
    guiding the pin into a notch in the tibial component to link the tibial component and the femoral component.

4. The method of claim 3, wherein the notch is located on an alignment tab that projects outward beyond an edge periphery region of the tibial component.

5. The method of claim 1, wherein inserting a pin into the femoral component comprises inserting the pin into a pin port in a condylar portion of the femoral component located offset from a medial-lateral center of an anterior side of the femoral component so that the pin projects anteriorly.

6. The method of claim 1, further comprising evaluating joint tension between the tibia and femur before locking the pin in engagement with the tibial component.

7. The method of claim 6, wherein evaluating joint tension between the tibia and femur comprises determining if joint tension in the knee joint replicates natural tension of the knee joint.

8. The method of claim 6, wherein evaluating joint tension between the tibia and femur further comprises inserting tibial components of different thicknesses into the anterior opening between resections of the tibia and femur.

9. The method of claim 8, wherein evaluating joint tension between the tibia and femur further comprises:
    assembly tibial components of different thicknesses to a tibial sizing plate to form an assembly; and
    inserting the assembly the anterior opening between resections of the tibia and femur.

10. The method of claim 8, evaluating joint tension between the tibia and femur further comprises:
    inserting tibial provisional components of different thicknesses into the anterior opening between resections of the tibia and femur.

11. The method of claim 8, wherein evaluating joint tension between the tibia and femur further comprises:
    assembling tibial plates of different thicknesses to a tibial provisional component at a pivot coupling to form an assembly; and
    inserting the assembly into the anterior opening between resections of the tibia and femur.

12. The method of claim 1, wherein the tibial component comprises:
    a tibial sizing plate comprising a base having sidewall that that can be attached to the resected tibial surface; and
    a tibial provisional component comprising one of a plurality of tibial provisional components that can be attached to the tibial sizing plate and that has a condylar surface to engage the femoral component, wherein each tibial provisional component of the plurality of tibial provisional components has a different thickness.

13. The method of claim 1, wherein the tibial component comprises:
    a tibial provisional component comprising:
    a femoral engagement surface contoured to engage with femoral condyles; and
    a tibial engagement surface comprising a planar surface;
    wherein the tibial provisional component is one of a plurality of tibial provisional components, wherein each tibial provisional component of the plurality of tibial provisional components has a different thickness.

14. The method of claim 1, wherein the tibial component comprises:
    a tibial sizing plate comprising:
    a lower surface comprising a planar surface; and
    an upper surface comprising a pivot mount; and
    a tibial provisional component comprising one of a plurality of tibial provisional components that can be rotatably attached to the pivot mount and that has a condylar surface to engage the femoral component, wherein each tibial provisional component of the plurality of tibial provisional components has a different thickness.

15. The method of claim 1, wherein inserting the tibial component into the anterior opening between resections of the tibia and femur comprises engaging a tibial condylar surface of the tibial component with femoral condyles of the femoral component.

16. The method of claim 1, wherein extending the tibia into extension so the tibia rotates against the tibial component further comprises sliding the tibial component against the femoral component.

17. The method of claim 1, wherein marking the location of the femur on the tibia comprises: using a pen or Bovie to mark a point on the tibia.

18. The method of claim 1, wherein:
identifying the location of the femur at the indicator on the tibial component comprises identifying a center of the femur; and
marking the location of the femur on the tibia using the indicator comprises marking the center of the tibia.

19. The method of claim 18, further comprising:
identifying a second location of the femur at a second indicator on the tibial component; and
marking the second location of the femur on the tibia using the second indicator.

20. The method of claim 1, further comprising:
removing the tibial component from the resected tibial surface; and
assembling a prosthetic tibial component with the resected tibial surface so that a location on the prosthetic tibial component aligns with the location of the femur on the tibia at the location marked on the tibia.

\* \* \* \* \*